(12) United States Patent
Bousamra et al.

(10) Patent No.: US 10,368,745 B2
(45) Date of Patent: *Aug. 6, 2019

(54) SYSTEMS AND METHODS FOR OPTIMIZING INSULIN DOSAGE

(71) Applicant: Roche Diabetes Care, Inc., Indianapolis, IN (US)

(72) Inventors: Steven Bousamra, Carmel, IN (US); Stefan Weinert, Pendleton, IN (US); Juergen Rasch-Menges, Schwetzingen (DE); P. Douglas Walling, Indianapolis, IN (US); John F. Price, McCordsville, IN (US); Heino Eikmeier, Lorsch (DE); Birgit Kraeling, Fussgoenheim (DE); Karl Werner, Wiesloch (DE); Ulrich Porsch, Weinheim (DE)

(73) Assignee: ROCHE DIABETES CARE INC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/887,239

(22) Filed: Feb. 2, 2018

(65) Prior Publication Data

US 2018/0168448 A1  Jun. 21, 2018

Related U.S. Application Data

(63) Continuation of application No. 12/818,310, filed on Jun. 18, 2010, now Pat. No. 9,918,635, which is a
(Continued)

(51) Int. Cl.
*A61B 5/02* (2006.01)
*A61B 5/00* (2006.01)
(Continued)

(52) U.S. Cl.
CPC ........ *A61B 5/0002* (2013.01); *A61B 5/14532* (2013.01); *A61B 5/14546* (2013.01);
(Continued)

(58) Field of Classification Search
CPC ... A61B 5/05; A61B 5/14532; A61B 5/14546; A61M 2230/201; C12Q 1/006
See application file for complete search history.

(56) References Cited

U.S. PATENT DOCUMENTS

| 4,151,845 A | 5/1979 | Clemens |
| 4,731,726 A | 3/1988 | Allen, III |

(Continued)

FOREIGN PATENT DOCUMENTS

| CN | 1130006 A | 8/1996 |
| CN | 1326162 A | 12/2001 |
| CN | 1755700 A | 4/2006 |
| CN | 1871783 A | 11/2006 |

(Continued)

OTHER PUBLICATIONS

Huang Elbert S., "The key to preventing burnout: understanding the burden of diabetes treatment", DiabetesVoice, vol. 53 Issue 3, pp. 33-35, Dec. 2008.
(Continued)

*Primary Examiner* — Puya Agahi
(74) *Attorney, Agent, or Firm* — Dinsmore & Shohl LLP

(57) ABSTRACT

Embodiments of a testing method for diabetics to optimize their administered insulin dosage comprise collecting sampling sets of biomarker data, each sampling set comprising a sufficient plurality of non-adverse sampling instances and each sampling instance comprising an acceptable biomarker reading at a single point in time recorded upon compliance with adherence criteria, determining a biomarker sampling parameter from each sampling set, comparing the biomarker sampling parameter to a target biomarker range, calculating an insulin adjustment parameter associated with the bio-
(Continued)

marker sampling parameter if the biomarker sampling parameter falls outside the target biomarker range, adjusting the insulin dosage by the insulin adjustment parameter if the biomarker sampling parameter falls outside the target biomarker range and the insulin dosage does not exceed maximum dosage, and exiting the testing method if the adjusted insulin dosage is optimized. The insulin dosage is optimized when biomarker sampling parameters fall within the target biomarker range.

20 Claims, 9 Drawing Sheets

Related U.S. Application Data continuation-in-part of application No. 12/643,338, filed on Dec. 21, 2009.

(60) Provisional application No. 61/140,270, filed on Dec. 23, 2008.

(51) Int. Cl.
    *A61B 5/145*     (2006.01)
    *G06F 19/00*     (2018.01)
    *G16H 10/20*     (2018.01)
    *G16H 20/17*     (2018.01)
    *G16H 80/00*     (2018.01)
    *G16H 10/40*     (2018.01)
    *A61M 31/00*     (2006.01)
    *A61B 5/05*     (2006.01)
    *C12Q 1/00*     (2006.01)

(52) U.S. Cl.
CPC ...... *G06F 19/3418* (2013.01); *G06F 19/3456* (2013.01); *G16H 10/20* (2018.01); *G16H 10/40* (2018.01); *G16H 20/17* (2018.01); *G16H 80/00* (2018.01); *A61B 5/05* (2013.01); *A61M 31/00* (2013.01); *A61M 2230/201* (2013.01); *C12Q 1/006* (2013.01)

(56) References Cited

U.S. PATENT DOCUMENTS

| | | |
|---|---|---|
| 4,803,625 A | 2/1989 | Fu et al. |
| 5,364,346 A | 11/1994 | Schrezenmeir |
| 5,377,258 A | 12/1994 | Bro |
| 5,572,421 A | 11/1996 | Altman et al. |
| 5,576,952 A | 11/1996 | Stutman et al. |
| 5,665,065 A | 9/1997 | Colman et al. |
| 5,722,418 A | 3/1998 | Bro |
| 5,822,715 A | 10/1998 | Worthington et al. |
| 5,840,020 A | 11/1998 | Heinonen et al. |
| 5,868,669 A | 2/1999 | Iliff |
| 5,879,163 A | 3/1999 | Brown et al. |
| 5,897,493 A | 4/1999 | Brown |
| 5,971,922 A | 10/1999 | Arita et al. |
| 5,997,475 A | 12/1999 | Bortz |
| 6,018,713 A | 1/2000 | Coli et al. |
| 6,024,699 A | 2/2000 | Surwit et al. |
| 6,039,688 A | 3/2000 | Douglas et al. |
| 6,108,665 A | 8/2000 | Bair et al. |
| 6,234,964 B1 | 5/2001 | Iliff |
| 6,241,633 B1 | 6/2001 | Conroy |
| 6,269,314 B1 | 7/2001 | Iitawaki et al. |
| 6,326,160 B1 | 12/2001 | Dunn et al. |
| 6,338,039 B1 | 1/2002 | Lonski et al. |
| 6,352,505 B1 | 3/2002 | Bortz |
| 6,379,301 B1 | 4/2002 | Worthington et al. |
| 6,424,847 B1 | 7/2002 | Mastrototaro et al. |
| 6,425,863 B1 | 7/2002 | Werner et al. |
| 6,544,212 B2 | 4/2003 | Galley et al. |
| 6,567,785 B2 | 5/2003 | Clendenon |
| 6,575,900 B1 | 6/2003 | Zweig et al. |
| 6,588,670 B2 | 7/2003 | Bukowski |
| 6,645,368 B1 | 11/2003 | Beaty et al. |
| 6,656,114 B1 | 12/2003 | Poulsen et al. |
| 6,691,043 B2 | 2/2004 | Ribeiro |
| 6,770,029 B2 | 8/2004 | Iliff |
| 6,835,175 B1 | 12/2004 | Porumbescu |
| 6,879,970 B2 | 4/2005 | Shiffman et al. |
| 6,923,763 B1 | 8/2005 | Kovatchev et al. |
| 6,954,662 B2 | 10/2005 | Freger et al. |
| 7,179,226 B2 | 2/2007 | Crothall et al. |
| 7,229,430 B2 | 6/2007 | Hickle et al. |
| 7,241,265 B2 | 7/2007 | Cummings et al. |
| 7,266,400 B2 | 9/2007 | Fine et al. |
| 7,278,983 B2 | 10/2007 | Ireland et al. |
| 7,291,107 B2 | 11/2007 | Hellwig et al. |
| 7,381,523 B2 | 6/2008 | Efendic |
| 7,389,133 B1 | 6/2008 | Kotulla et al. |
| 7,404,796 B2 | 7/2008 | Ginsberg |
| 7,405,196 B2 | 7/2008 | Rosskamp et al. |
| 7,412,395 B2 | 8/2008 | Rowlandson |
| 7,413,749 B2 | 8/2008 | Wright et al. |
| 7,415,447 B2 | 8/2008 | Shiffman et al. |
| 7,509,156 B2 | 3/2009 | Flanders |
| 7,523,040 B2 | 4/2009 | Kirchhoff et al. |
| 7,553,281 B2 | 6/2009 | Hellwig et al. |
| 7,584,108 B2 * | 9/2009 | Brown ............... G06F 19/3418 705/2 |
| 7,676,329 B2 | 3/2010 | Garczarek et al. |
| 7,685,000 B1 | 3/2010 | Petit et al. |
| 7,734,323 B2 | 6/2010 | Blomquist et al. |
| 7,761,310 B2 | 7/2010 | Rodgers |
| 7,766,830 B2 | 8/2010 | Fox et al. |
| 8,078,592 B2 | 12/2011 | Gejdos et al. |
| 8,117,020 B2 | 2/2012 | Abensour et al. |
| 8,131,472 B2 | 3/2012 | Chow et al. |
| 2002/0019752 A1 | 2/2002 | Takase |
| 2002/0059030 A1 | 5/2002 | Otworth et al. |
| 2002/0107476 A1 | 8/2002 | Mann et al. |
| 2002/0143563 A1 | 10/2002 | Hufford et al. |
| 2002/0161288 A1 | 10/2002 | Shin et al. |
| 2003/0028399 A1 | 2/2003 | Davis et al. |
| 2003/0104982 A1 | 6/2003 | Wittmann et al. |
| 2003/0130616 A1 | 7/2003 | Steil et al. |
| 2003/0163223 A1 | 8/2003 | Blomquist |
| 2003/0208113 A1 | 11/2003 | Mault et al. |
| 2003/0211617 A1 | 11/2003 | Jones |
| 2003/0229517 A1 | 12/2003 | Meserol et al. |
| 2004/0078065 A1 | 4/2004 | Kroll |
| 2004/0122701 A1 | 6/2004 | Dahlin et al. |
| 2004/0122709 A1 | 6/2004 | Avinash et al. |
| 2004/0172284 A1 | 9/2004 | Sullivan et al. |
| 2004/0243443 A1 | 12/2004 | Asano et al. |
| 2004/0247748 A1 | 12/2004 | Bronkema |
| 2005/0010416 A1 | 1/2005 | Anderson et al. |
| 2005/0016844 A1 | 1/2005 | Burke et al. |
| 2005/0020903 A1 | 1/2005 | Krishnan et al. |
| 2005/0021372 A1 | 1/2005 | Mikkelsen et al. |
| 2005/0049179 A1 | 3/2005 | Davidson et al. |
| 2005/0075553 A1 | 4/2005 | Sakai et al. |
| 2005/0119540 A1 | 6/2005 | Potts et al. |
| 2005/0119788 A1 | 6/2005 | Engleson et al. |
| 2006/0010014 A1 | 1/2006 | Brown |
| 2006/0010098 A1 | 1/2006 | Goodnow et al. |
| 2006/0025931 A1 | 2/2006 | Rosen et al. |
| 2006/0030890 A1 | 2/2006 | Cosentino et al. |
| 2006/0031094 A1 | 2/2006 | Cohen et al. |
| 2006/0047192 A1 | 3/2006 | Hellwig et al. |
| 2006/0137695 A1 | 6/2006 | Hellwig et al. |
| 2006/0142651 A1 * | 6/2006 | Brister ............... A61B 5/0031 600/347 |
| 2006/0171503 A1 | 8/2006 | O'Hara et al. |
| 2006/0173406 A1 | 8/2006 | Hayes et al. |
| 2006/0173409 A1 | 8/2006 | Yang |
| 2006/0195022 A1 | 8/2006 | Trepagnier et al. |
| 2006/0195029 A1 * | 8/2006 | Shults ............... A61B 5/0002 600/345 |
| 2006/0195342 A1 | 8/2006 | Khan et al. |

(56) References Cited

U.S. PATENT DOCUMENTS

| | | |
|---|---|---|
| 2006/0253296 A1 | 11/2006 | Liisberg et al. |
| 2006/0271404 A1 | 11/2006 | Brown |
| 2006/0287883 A1 | 12/2006 | Turgiss et al. |
| 2007/0038472 A1 | 2/2007 | Finken et al. |
| 2007/0048691 A1 | 3/2007 | Brown |
| 2007/0055483 A1 | 3/2007 | Lee et al. |
| 2007/0060796 A1 | 3/2007 | Kim |
| 2007/0100659 A1 | 5/2007 | Preiss |
| 2007/0106135 A1 | 5/2007 | Sloan et al. |
| 2007/0116329 A1 | 5/2007 | Tsubata |
| 2007/0162304 A1 | 7/2007 | Rodgers |
| 2007/0198296 A1 | 8/2007 | Pellinat et al. |
| 2007/0213604 A1 | 9/2007 | Brown |
| 2007/0230282 A1 | 10/2007 | May et al. |
| 2007/0253904 A1 | 11/2007 | Gunton et al. |
| 2007/0282636 A1 | 12/2007 | Sauk et al. |
| 2008/0021287 A1 | 1/2008 | Woellenstein et al. |
| 2008/0025591 A1 | 1/2008 | Bhanot et al. |
| 2008/0058628 A1 | 3/2008 | Hellwig et al. |
| 2008/0097793 A1 | 4/2008 | Dicks et al. |
| 2008/0109043 A1 | 5/2008 | Salo et al. |
| 2008/0125636 A1 | 5/2008 | Ward et al. |
| 2008/0146895 A1 | 6/2008 | Olson et al. |
| 2008/0154513 A1 | 6/2008 | Kovatchev et al. |
| 2008/0172027 A1 | 7/2008 | Blomquist |
| 2008/0177119 A1 | 7/2008 | Juttu et al. |
| 2008/0177149 A1 | 7/2008 | Weinert et al. |
| 2008/0177165 A1 | 7/2008 | Blomquist et al. |
| 2008/0183494 A1 | 7/2008 | Cuddihy et al. |
| 2008/0201325 A1 | 8/2008 | Doniger et al. |
| 2008/0206799 A1 | 8/2008 | Blomquist |
| 2008/0214919 A1 | 9/2008 | Harmon et al. |
| 2008/0220403 A1* | 9/2008 | Marling ............... G06F 19/00 434/262 |
| 2008/0228045 A1 | 9/2008 | Gao et al. |
| 2008/0228056 A1 | 9/2008 | Blomquist et al. |
| 2008/0234943 A1 | 9/2008 | Ray et al. |
| 2008/0234992 A1 | 9/2008 | Ray et al. |
| 2008/0243902 A1 | 10/2008 | Rong et al. |
| 2008/0255438 A1 | 10/2008 | Saidara et al. |
| 2008/0262745 A1 | 10/2008 | Polidori |
| 2008/0269585 A1 | 10/2008 | Ginsberg |
| 2008/0300534 A1 | 12/2008 | Blomquist |
| 2008/0306353 A1 | 12/2008 | Douglas et al. |
| 2008/0306434 A1* | 12/2008 | Dobbles ............... A61B 5/0002 604/66 |
| 2008/0319384 A1 | 12/2008 | Yodfat et al. |
| 2009/0006061 A1 | 1/2009 | Thukral et al. |
| 2009/0018406 A1 | 1/2009 | Yodfat et al. |
| 2009/0028208 A1 | 1/2009 | Martin |
| 2009/0112882 A1 | 4/2009 | Maresh et al. |
| 2009/0132284 A1 | 5/2009 | Fey et al. |
| 2009/0150177 A1 | 6/2009 | Buck et al. |
| 2009/0150186 A1 | 6/2009 | Cohen et al. |
| 2009/0164239 A1 | 6/2009 | Hayter et al. |
| 2009/0176692 A1 | 7/2009 | Habermann et al. |
| 2009/0177147 A1 | 7/2009 | Blomquist et al. |
| 2009/0228435 A1 | 9/2009 | Dattathreya |
| 2009/0234262 A1 | 9/2009 | Reid, Jr. et al. |
| 2009/0234674 A1 | 9/2009 | Wurster |
| 2009/0240520 A1 | 9/2009 | Takano et al. |
| 2009/0247836 A1 | 10/2009 | Cole et al. |
| 2009/0253970 A1 | 10/2009 | Bashan et al. |
| 2009/0253973 A1 | 10/2009 | Bashan et al. |
| 2009/0281392 A1 | 11/2009 | Brown |
| 2009/0281393 A1 | 11/2009 | Smith |
| 2010/0016700 A1 | 1/2010 | Sieh et al. |
| 2010/0069730 A1 | 3/2010 | Bergstrom et al. |
| 2010/0138197 A1 | 6/2010 | Sher |
| 2010/0141656 A1 | 6/2010 | Krieftewirth |
| 2010/0160757 A1 | 6/2010 | Weinert et al. |
| 2010/0160759 A1 | 6/2010 | Celentano et al. |
| 2010/0168660 A1 | 7/2010 | Galley et al. |
| 2010/0174553 A1 | 7/2010 | Kaufman et al. |
| 2010/0184565 A1 | 7/2010 | Avellino |
| 2010/0198142 A1 | 8/2010 | Sloan et al. |
| 2010/0198520 A1 | 8/2010 | Breton et al. |
| 2010/0212675 A1 | 8/2010 | Walling et al. |
| 2010/0218132 A1 | 8/2010 | Soni et al. |
| 2010/0222765 A1 | 9/2010 | Blomquist et al. |
| 2010/0262434 A1 | 10/2010 | Shaya |
| 2010/0265073 A1 | 10/2010 | Harper |
| 2010/0274497 A1 | 10/2010 | Rush |
| 2010/0330598 A1 | 12/2010 | Thukral et al. |
| 2010/0331650 A1 | 12/2010 | Batman et al. |
| 2010/0331651 A1 | 12/2010 | Groll |
| 2011/0071365 A1 | 3/2011 | Lee et al. |
| 2011/0144463 A1 | 6/2011 | Pesach et al. |
| 2012/0226117 A1 | 9/2012 | Lamego et al. |
| 2016/0047192 A1 | 2/2016 | Arteaga |

FOREIGN PATENT DOCUMENTS

| | | |
|---|---|---|
| CN | 1914615 A | 2/2007 |
| CN | 101325906 A | 12/2008 |
| CN | 101667224 A | 3/2010 |
| DE | 102005041627 A1 | 3/2007 |
| EP | 1702559 A2 | 9/2006 |
| EP | 1728469 A2 | 12/2006 |
| EP | 1956508 A2 | 8/2008 |
| EP | 2006786 A1 | 12/2008 |
| FR | 2760962 A1 | 9/1998 |
| JP | 2001000397 A | 1/2001 |
| JP | 2002175372 A | 6/2002 |
| JP | 2003204941 A | 7/2003 |
| JP | 2005011329 A | 1/2005 |
| JP | 2005110920 A | 4/2005 |
| JP | 2007143623 A | 6/2007 |
| JP | 2008506468 A | 3/2008 |
| WO | 9420916 A1 | 9/1994 |
| WO | 9901836 A1 | 1/1999 |
| WO | 0009007 A1 | 2/2000 |
| WO | 0042907 A1 | 7/2000 |
| WO | 0122343 A2 | 3/2001 |
| WO | 0128416 A1 | 4/2001 |
| WO | 0133314 A2 | 5/2001 |
| WO | 0152727 A1 | 7/2001 |
| WO | 03002258 A1 | 1/2003 |
| WO | 03046695 A2 | 6/2003 |
| WO | 03082096 A1 | 10/2003 |
| WO | 03088962 A1 | 10/2003 |
| WO | 2004015539 A2 | 2/2004 |
| WO | 2004084820 A2 | 10/2004 |
| WO | 2004114184 A1 | 12/2004 |
| WO | 2007081853 A2 | 7/2007 |
| WO | 2007117719 A2 | 10/2007 |
| WO | 2007144419 A2 | 12/2007 |
| WO | 2007149319 A2 | 12/2007 |
| WO | 2008091320 A2 | 7/2008 |
| WO | 2008105859 A1 | 9/2008 |
| WO | 2008114863 A1 | 9/2008 |
| WO | 2008131324 A1 | 10/2008 |
| WO | 2009009528 A2 | 1/2009 |
| WO | 2009013637 A2 | 1/2009 |
| WO | 2009075925 A1 | 6/2009 |
| WO | 2009146119 A2 | 12/2009 |
| WO | 2010000266 A1 | 1/2010 |
| WO | 2010039743 A1 | 4/2010 |
| WO | 2010063758 A1 | 6/2010 |
| WO | 2010072387 A2 | 7/2010 |
| WO | 2010075350 A1 | 7/2010 |
| WO | 2010089304 A1 | 8/2010 |
| WO | 2010089305 A1 | 8/2010 |
| WO | 2010089306 A1 | 8/2010 |
| WO | 2010089307 A1 | 8/2010 |
| WO | 2010097796 A1 | 9/2010 |

OTHER PUBLICATIONS

Larimer et al., "Relapse Prevention, an Overview of Marlatt's Cognitive-Behavioral Model", Alcohol Research & Health, vol. 23, No. 2, pp. 151-160 (1999).

(56) References Cited

OTHER PUBLICATIONS

Marlatt et al., "Clinical Guidelines for Imlementing Relapse Prevention Therapy", Addictive Behaviors Research Center/University of Washington, pp. 1-49, Dec. 2002.
Montani et al., "Managing diabetic patients through a Multi Modal Reasoning Methodology", International Journal of Medical Informatics, vol. 58, Complete, pp. 243-256, Sep. 1, 2000.
Schmidt et al, "Case-based Reasoning for Medical Knowledge-Based Systems", Institute for Medial Informatics and Biometry, University of Rostock Rembrandtstr, 16/17, D-18055, Rostock, Germany, 2000.
Denis Raccah, "Insulin therapy in patients with type 2 diabetes mellitus: Treatment to target fasting and postprandial blood glucose levels", Insulin 1:158-165 (2006).
Morgan et al., "Uncertainty a Guide to Dealing with Uncertainty in Quantitative Risk and Poly Analysis", Cambridge University Press, pp. 307-310 (1990).
Brand et al., "Updating uncertainty in an integrated risk assessment: Conceptual framework and methods", Risk Analysis 1995 US, vol. 15, No. 6, pp. 719-731 (1995).
Gerstein et al., "A randomized trial of adding insulin glargine v. avoidance of insulin in people with Type 2 diabetes on either no oral-glucose-lowering agents or submaximal doses of metformin and/or sulphonylureas. The Canadian Insight (Implementing New Strategies with Insulin Glargine for Hyperglycaemia Treatment) Study", Diabetic Medicine, vol. 23, pp. 736-742 (2006).
Hirsch et al., "A Real-World Approach to Insulin Therapy in Primary Care Practice", Practical Pointers, Clinical Diabetes, vol. 23, Nov. 2, 2005.
Nathan et al., "Medical Management of Hyperglycemia in Type 2 Diabetes: A Consensus Algorithm for the Initiation and Adjustment of Therapy", Diabetes Care, vol. 31, No. 12: pp. 1-11, Dec. 2008.
Riddle et al., "The Treat-to-Target Trial, Randomized addition of glargine or human NPH insulin to oral therapy of type 2 diabetic patients", Diabetes Care, vol. 26, No. 11: pp. 2080-3086, Nov. 2003.
De Groen et al., "Applying World Wide Web Technology to the Study of Patients with Rare Diseases", Annals of Internal Medicine, vol. 129, No. 2, 15.071998, pp. 107-113, XP002587966 (1998).
Accu-Chek Spirit Pump User Guide, Sep. 2008, pp. 1-201.
Accu-Chek Smart Pix Device Reader User's Manual, Sep. 2008, pp. 1-92.
Accu-Chek Aviva Blood Glucose Meter Owner's Booklet, Sep. 2008, pp. 1-92.
Accu-Chek Spirit Insulin Pump System, Pocket Compass Software with Bolus Calculator User Guide, Oct. 2005, pp. 1-174.
Glooko app Offers Diabetics Easier Self-Checks, www.phys.org/news/2011-11-glooko-app-diabetics-easier-self-checks.html (2011).
Glooko Logbook & MeterSync Cable, www. glooko.com/product/logbook (2011).
Smiths Medical MD, Inc., Deltec Cozmo® Fine Tuning Your Deltec Cozmo® Insulin Pump Settings, Overnight Basal Rate Test Instructions, 2 pp, date unknown.
Smiths Medical MD, Inc., Deltec Cozmo®, User Maual, Deltec Cozmo® Insulin Pump, 245 pp, date unknown.
Montani et al., "Integrating Case Based and Rule Based Reasoning in a Decision Support System: Evaluation with Simulated Patients", AMIA, Inc., pp. 887-891, 1999.
Breton, M. et al., "Analysis, Modeling, and Simulation of the Accuracy of Continuous Glucose Sensors", Journal of Diabetes Science and Technology; Sep. 2008, pp. 853-862, vol. 2, Issue 5, Diabetes Technology Society.
Munro et al., "Association Between Medication Regimen Complexity and Achievement of Therapeutic Goals in Patients with Type 2 Diabetes", School of Pharmacy, The Robert Gordon University, Aberdeen, AB10 1 FR (k.munroe@rgu.ac.uk) pp. 1, 2, date unknown.
Lustria et al., "Computer-Tailored Health Interventions Delivered Over the Web: Review and Analysis of Key Components", U.S. National Library of Medicine, National Institute of Health, p. 1, 2009.
Joslin Diabetes Center & Joslin Clinic, "Clinical Guideline for Adults with Diabetes", pp. 1-13, May 21, 2010.
Joslin Diabetes Center & Joslin Clinic, "Clinical Guideline for Pharmacological Management of Type 2 Diabetes", pp. 1-9, Jan. 12, 2007.
Pollack et al., "Impact of Treatment Complexity on Adherence and Glycemic Control: An Analysis of Oral Antidiabetic Agents", www.j.comjournal.com, vol. 17, No. 6, pp. 257-265, Jun. 2010.
Ingersoll et al., "The Impact of Medication Regimen Factors on Adherence to Chronic Treatment: a Review of Literature", NIH Public Access, Author Manuscript, J. Behav Med. Jun. 2008; 31(3): 213-224, doi: 10.1007/s10865-007-9147-y; pp. 1-16.
Crowe et al., "Time Synching or Time Sinking?", Diabetes Technology & Therapeutics, vol. 7, No. 5, 2005.
Accu-Chek 360 Diabetes Management System, pp. 1-2, Aug. 24, 2010.
Accu-Chek Pocket Compass Software with Bolus Calculator User Guide, p. 1-174, Oct. 2005.
Non-Final Office Action dated Apr. 19, 2018, pertaining to U.S. Appl. No. 14/252,052, filed Apr. 14, 2014.
Non-Final Office Action for U.S. Appl. No. 12/643,338 dated Aug. 4, 2018.
Office Action dated Sep. 13, 2016 filed in corresponding Canadian Case, Application No. 2,747,309.
Final Office Action regarding U.S. Appl. No. 12/818,894 dated Sep. 9, 2016.
USPTO Non Final Rejection dated Dec. 18, 2013 in reference to co-pending U.S. Appl. No. 12/818,310, filed Jun. 18, 2010.
USPTO Non Final Rejection dated Feb. 21, 2014 in reference to co-pending U.S. Appl. No. 12/818,894, filed Jun. 18, 2010.
Non-final Office Action pertaining to U.S. Appl. No. 13/107,436, dated May 31, 2013.
Final Office Action pertaining to U.S. Appl. No. 12/643,415, dated May 17, 2013.
Final Office Action regarding U.S. Appl. No. 12/818,930 dated Mar. 15, 2013.
International Preliminary Report on Patentability completed Nov. 13, 2012 pertaining to International Application No. PCT/EP2011/002925.
Final Office Action pertaining to U.S. Appl. No. 12/818,894 dated Nov. 21, 2012.
Non-final Office Action pertaining to U.S. Appl. No. 12/818,310, dated Sep. 26, 2012.
Final Office Action pertaining to U.S. Appl. No. 12/818,875 dated Sep. 28, 2012.
Non-final Office Action pertaining to U.S. Appl. No. 12/643,415 dated Sep. 13, 2012.
Non-final Office Action pertaining to U.S. Appl. No. 12/818,795 dated Sep. 6, 2012.
Non-final Office Action pertaining to U.S. Appl. No. 12/818,930, dated Aug. 27, 2012.
Non-final Office Action pertaining to U.S. Appl. No. 12/818,875, dated Apr. 2, 2012.
International Search Report, Application No. PCT/EP2009/009171 filed Dec. 21, 2009, completion of ISR is Jun. 21, 2010, pp. 1-14.
International Search Report, Application No. PCT/EP2009/009171 filed Dec. 21, 2009, completion of ISR is Sep. 24, 2010, pp. 1-24.
Dassau, et al., Detection of a Meal Using Continuous Glucose Monitoring, Diabetes Care, vol. 31, No. 2, Feb. 2008, pp. 295-300.

* cited by examiner

| | | | | | |
|---|---|---|---|---|---|
| 237a | 240a | 256a | 12/23/2009 8:00 | 1 | |
| 237b | 240b | 256b | 12/23/2009 9:00 | 2 | 5, 1 |
| 237c | 240c | 256c | 12/23/2009 9:30 | 3 | 5, 1 |
| 237d | 240d | 256d | 12/23/2009 10:00 | <null> | |
| ... | ... | ... | ... | ... | |
| 237n | 240n | 256n | mm/dd/yyyy hh:mm | n | |

FIG. 4

SYSTEMS AND METHODS FOR OPTIMIZING INSULIN DOSAGE

CROSS-REFERENCE TO RELATED APPLICATIONS

The present application is a continuation of U.S. patent application Ser. No. 12/818,310 filed Jun. 18, 2010, which is a continuation in part of U.S. patent application Ser. No. 12/643,338 filed Dec. 21, 2009, which claims priority to U.S. Provisional Application Ser. No. 61/140,270 filed Dec. 23, 2008, each of which are incorporated by reference herein in their entirety.

TECHNICAL FIELD

Embodiments of the present disclosure relate generally to diabetes management, and particularly to methods and systems for diabetic persons to optimize their administered insulin dosage.

BACKGROUND

A disease which is long lasting or which reoccurs often is defined typically as a chronic disease. Known chronic diseases include, among others, depression, compulsive obsession disorder, alcoholism, asthma, autoimmune diseases (e.g., ulcerative colitis, lupus erythematosus), osteoporosis, cancer, and diabetes mellitus. Such chronic diseases require chronic care management for effective long-term treatment. After an initial diagnosis, one of the functions of chronic care management is then to optimize a patient's therapy of the chronic disease.

In the example of diabetes mellitus, which is characterized by hyperglycemia resulting from inadequate insulin secretion, insulin action, or both, it is known that diabetes manifests itself differently in each person because of each person's unique physiology that interacts with variable health and lifestyle factors such as diet, weight, stress, illness, sleep, exercise, and medication intake.

Biomarkers are patient biologically derived indicators of biological or pathogenic processes, pharmacologic responses, events or conditions (e.g., aging, disease or illness risk, presence or progression, etc.). For example, a biomarker can be an objective measurement of a variable related to a disease, which may serve as an indicator or predictor of that disease. In the case of diabetes mellitus, such biomarkers include measured values for glucose, lipids, triglycerides, and the like. A biomarker can also be a set of parameters from which to infer the presence or risk of a disease, rather than a measured value of the disease itself. When properly collected and evaluated, biomarkers can provide useful information related to a medical question about the patient, as well as be used as part of a medical assessment, as a medical control, and/or for medical optimization.

For diabetes, clinicians generally treat diabetic persons according to published therapeutic guidelines such as, for example, Joslin Diabetes Center & Joslin Clinic, *Clinical Guideline for Pharmacological Management of Type 2 Diabetes* (2007) and Joslin Diabetes Center & Joslin Clinic, *Clinical Guideline for Adults with Diabetes* (2008). The guidelines may specify a desired biomarker value, e.g., a fasting blood glucose value of less than 100 mg/dl, or the clinician can specify a desired biomarker value based on the clinician's training and experience in treating patients with diabetes.

However, such guidelines do not specify biomarker collection procedures for parameter adjustments to support specific therapies used in optimizing a diabetic person's therapy. Subsequently, diabetic persons often must measure their glucose levels with little structure for collection and with little regard to lifestyle factors. Specifically, a host of issues have been identified for the titration of basal insulin. The root cause of these issues is a lack of a centralized location that tells the patient the specific dosage of insulin to take—both during the titration optimization phase, as well as post optimization—daily use. The issues may include the following: patients taking only the amount on the label attached to the packaging as originally prescribed by the physician; patients eating before sampling their blood glucose rendering the sample instance unusable or inappropriate; patients forgetting to take the samples at the appropriate time; patients refusing to take more than the minimal amount due to fear; and not understanding the instructions from the physician.

It is desirable to include a parameterized testing method for the implementation of most known basal rate titration algorithms, permitting the creation of structured centralized testing procedures to assist the patient in insulin titration.

SUMMARY

It is against the above background that the present testing method embodiments suitable for diabetic persons to optimize their administered insulin dosage are provided. These embodiments for optimizing the titration of insulin, specifically, basal insulin, helps a patient and physician determine an insulin level that consistently results in fasting blood glucose values within a predetermined range, and without adverse events (e.g., hypoglycemic events or hyperglycemic events of varying severity) occurring at any time of the day. The testing method embodiments provide customized systems and methods which provides guidance and confidence to patient during titration of insulin. The testing methods benefit physicians by providing a monitored implementation of their standardized practices, which yields higher confidence in the outcome of the titration. Additionally, the testing methods are also anticipated to reduce the cost of optimization by reducing the number of required office visits necessary to support the person in conducting the testing method.

Embodiments of the disclosure can be implemented, for example, as follows: a paper tool; diabetes software integrated into a collection device such as a blood glucose meter; diabetes software integrated into a personal digital assistant, handheld computer, or mobile phone; diabetes software integrated into a device reader coupled to a computer; diabetes software operating on a computer such as a personal computer; and diabetes software accessed remotely through the internet.

In one embodiment, a testing method suitable for a diabetic person to optimize an administered insulin dosage includes providing a structured collection procedure from a server of a health care provider to a collection device configured to guide the diabetic person through the structured collection procedure and optimize the administered insulin dosage. The collection device comprises a meter configured to measure one or more selected biomarkers, a processor disposed inside the meter and coupled to a memory, wherein the memory stores the structured collection procedure provided from the server, and software having instructions that when executed by the processor causes the processor to instruct the diabetic person to collect one or more sampling sets of biomarker data in accordance with the structured collection procedure. The server is a central repository for a plurality of the structured collection procedures. The method further includes executing the software on the collection device and according to instructions and timing provided by the structured collection procedure: collecting one or more sampling sets of biomarker data. Each of the one or more sampling sets comprises a plurality of sampling instances recorded over a collection period and each sampling instance of the plurality of sampling instances comprises an acceptable biomarker reading recorded upon compliance with one or more acceptance criterion based on at least one of a schedule-based action or a patient-based action and that is applied to the one or more sampling sets of biomarker data. After each collection of the one or more sampling sets of biomarker data, said processor performs the processes of: determining a biomarker sampling parameter from the one or more sampling sets of biomarker data whereby only these biomarker data are considered which are in compliance with the one or more acceptance criterion, comparing the biomarker sampling parameter to a target biomarker range, calculating an insulin adjustment parameter associated with the biomarker sampling parameter in response to the biomarker sampling parameter falling outside the target biomarker range, adjusting an insulin dosage by an amount of the insulin adjustment parameter in response to the biomarker sampling parameter falling outside the target biomarker range and in response to the insulin dosage not exceeding maximum dosage, and exiting the testing method in response to the adjusted insulin dosage being optimized as an optimized insulin dosage such that the optimized insulin dosage is administered as the administered insulin dosage, otherwise repeating with a next sampling set of the one or more sampling sets of biomarker data, the optimized insulin dosage being achieved when the one or more biomarker sampling parameters fall within the target biomarker range.

In another embodiment, a testing method suitable for a diabetic person to optimize an administered insulin dosage includes providing a structured collection procedure from a server of a health care provider to a collection device configured to guide the diabetic person through the structured collection procedure and optimize the administered insulin dosage. The collection device comprises a meter configured to measure one or more selected biomarkers, a processor disposed inside the meter and coupled to a memory, wherein the memory stores the structured collection procedure provided from the server, and software having instructions that when executed by the processor causes the processor to instruct the diabetic person to collect one or more sampling sets of biomarker data in accordance with the structured collection procedure. The server is a central repository for a plurality of the structured collection procedures. The method further includes collecting one or more sampling sets of biomarker data by the collection device. Each of the one or more sampling sets comprises a plurality of sampling instances recorded over a collection period and each sampling instance of the plurality of sampling instances comprises an acceptable biomarker reading recorded upon compliance with one or more acceptance criterion based on at least one of a schedule-based action or a patient-based action and that is applied to the one or more sampling sets of biomarker data. The one or more acceptance criterion require collection of the acceptable biomarker reading by the diabetic patient at a time required by the collection device. After each collection of the one or more sampling sets of biomarker data, said processor performs the processes of: determining a biomarker sampling parameter from the one or more sampling sets of biomarker data whereby only these biomarker data are considered which are in compliance with the one or more acceptance criterion, comparing the biomarker sampling parameter to a target biomarker range, calculating an insulin adjustment parameter associated with the biomarker sampling parameter in response to the biomarker sampling parameter falling outside the target biomarker range, adjusting an insulin dosage by an amount of the insulin adjustment parameter in response to the biomarker sampling parameter falling outside the target biomarker range and in response to the insulin dosage not exceeding maximum dosage, and exiting the testing method in response to the adjusted insulin dosage being optimized as an optimized insulin dosage such that the optimized insulin dosage is administered as the administered insulin dosage, otherwise repeating with a next sampling set of the one or more sampling sets of biomarker data, the optimized insulin dosage being achieved when the one or more biomarker sampling parameters fall within the target biomarker range.

These and additional features provided by the embodiments described herein will be more fully understood in view of the following detailed description, in conjunction with the drawings. These and other advantages and features of the embodiments disclosed herein, will be made more apparent from the description, drawings and claims that follow.

BRIEF DESCRIPTION OF THE DRAWINGS

The following detailed description of the embodiments of the present disclosure can be best understood when read in conjunction with the following drawings, where like structure is indicated with like reference numerals.

FIG. 4 shows a depiction in tabular format of a data record embodiment created from using a structured testing method on the collection device of FIG. 3 according to the present disclosure.

DETAILED DESCRIPTION

Figure 1:
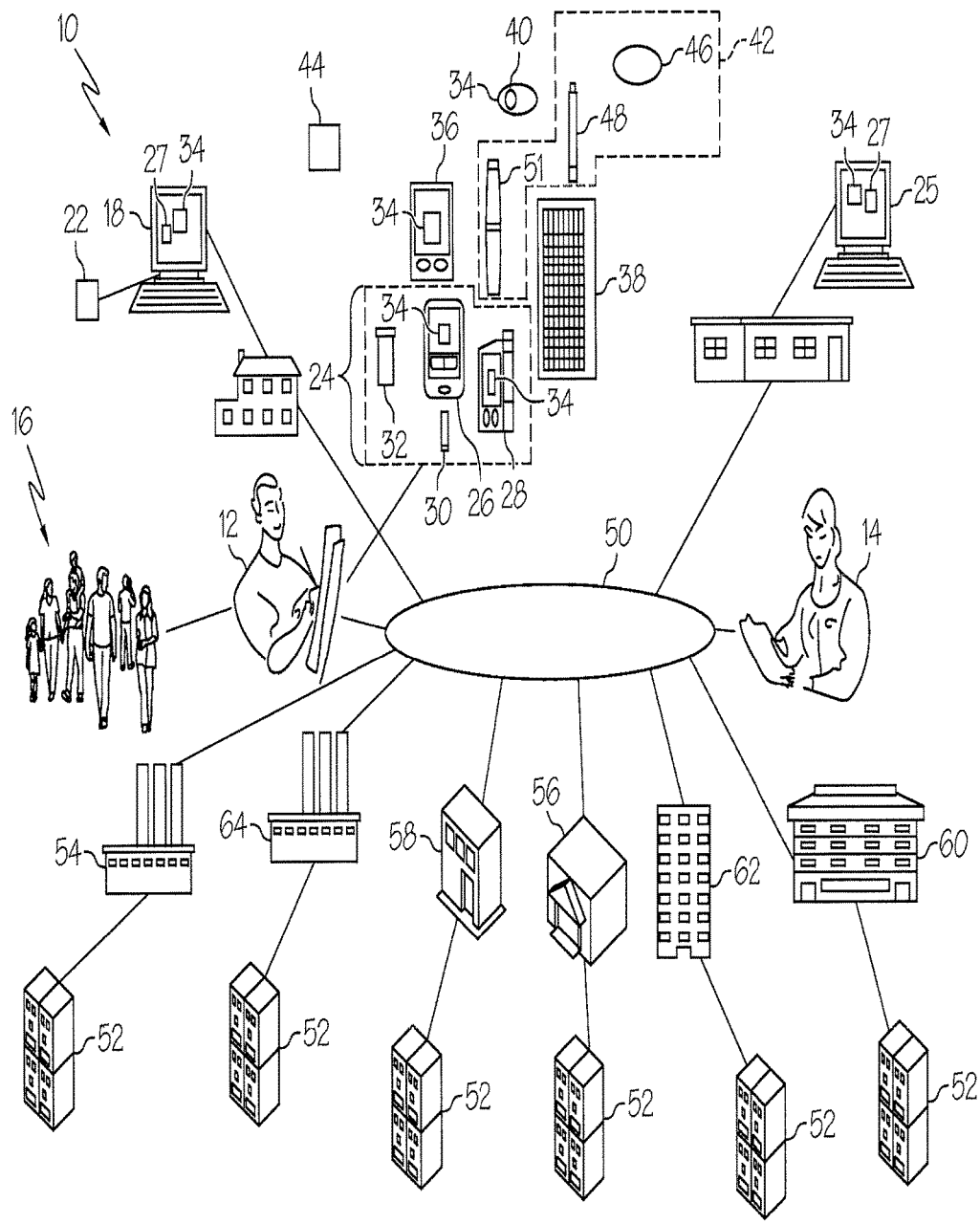
FIG. 1 is a diagram showing a chronic care management system for a diabetes patient and a clinician along with others having an interest in the chronic care management of the patient according to an embodiment of the present disclosure.

The present disclosure will be described below relative to various illustrative embodiments. Those skilled in the art will appreciate that the present disclosure may be implemented in a number of different applications and embodiments and is not specifically limited in its application to the particular embodiments depicted herein. In particular, the present disclosure will be discussed below in connection with diabetes management via sampling blood, although those of ordinary skill will recognize that the present disclosure could be modified to be used with other types of fluids or analytes besides glucose, and/or useful in managing other chronic diseases besides diabetes.

As used herein with the various illustrated embodiments described below, the follow terms include, but are not limited to, the following meanings.

The term "biomarker" can mean a physiological variable measured to provide data relevant to a patient such as for example, a blood glucose value, an interstitial glucose value, an HbA1c value, a heart rate measurement, a blood pressure measurement, lipids, triglycerides, cholesterol, and the like.

The term "contextualizing" can mean documenting and interrelating conditions that exists or will occur surrounding a collection of a specific biomarker measurement. Preferably, data about documenting and interrelating conditions that exists or will occur surrounding a collection of a specific biomarker are stored together with the collected biomarker data and are linked to it. In particular, a further assessment of the collected biomarker data takes into account the data about documenting and interrelating conditions so that not only the data as such are evaluated but also the link between data to which it is contextualized. The data about documenting and interrelating conditions can include for example information about the time, food and/or exercises which occurs surrounding a collection of a specific biomarker measurement and/or simultaneously thereto. For example, the context of a structured collection procedure according in an embodiment to the present disclosure can be documented by utilizing entry criterion for verifying a fasting state with the diabetic person before accepting a biomarker value during a Basal titration optimization focused testing procedure.

The term "contextualized biomarker data" can mean the information on the interrelated conditions in which a specific biomarker measurement was collected combined with the measured value for the specific biomarker. In particular, the biomarker data are stored together with the information on the interrelated conditions under which a specific biomarker measurement was collected and are linked thereto.

The term "biomarker sampling parameter" can mean the mathematical manipulation of the requisite number of collected, for example, non-adverse biomarker readings in a sampling set. The mathematical manipulation can be, for example, averaging sampling instances, summing the sampling instances, performing a graphical analysis on the sampling instances, performing a mathematical algorithm on the sampling set, or combinations thereof.

The term "criteria" can mean one or more criterions, and can be at least one or more of a guideline(s), rule(s), characteristic(s), and dimension(s) used to judge whether one or more conditions are satisfied or met to begin, accept, and/or end one or more procedural steps, actions, and/or values.

The term "adherence" can mean that a person following a structured collection procedure performs requested procedural steps appropriately. For example, the biomarker data should be measured under prescribed conditions of the structured collection procedure. If then the prescribed conditions are given for a biomarker measurement the adherence is defined as appropriate. For examples, the prescribed conditions are time related conditions and/or exemplarily can include eating of meals, taking a fasting sample, eating a type of meal with a requested window of time, taking a fasting sample at a requested time, sleeping a minimum amount of time, and the like. The adherence can be defined as appropriate or not appropriate for a structured collection procedure, a group of sample instances, or a single data point of a contextualized biomarker data. Preferably, the adherence can be defined as appropriate or not appropriate by a range of a prescribed condition(s) or by a selectively determined prescribed condition(s). Moreover the adherence can be calculated as a rate of adherence describing in which extent the adherence is given for a structured collection procedure or a single data point in particular of a contextualized biomarker data.

The term "adherence event" can mean when a person executing a structured collection procedure fails to perform a procedural step. For example, if a person did not collect data when requested by the collection device, the adherence is determined as not appropriate resulting in an adherence event. In another example, adherence criteria could be a first criterion for the patient to fast 6 hours and a second criterion for collecting a fasting bG value at a requested time. In this example, if the patient provides the bG sampling at the requested time but fasted only 3 hours before providing, then although the second adherence criterion is met, the first adherence criterion is not, and hence an adherence event for the first criterion would occur.

The term "violation event" is a form of an adherence event in which the person executing the structured collection (testing) procedure (protocol) does not administer a therapeutic at a recommended time, does not administer a recommended amount, or both.

The term "adherence criterion" can include adherence and can mean a basis for comparison (e.g., assessment) of a value/information related to a measured value and/or a calculated value with a defined value/information, or defined range of the values, wherein based on the comparison, data can be accepted with approval and positive reception. Adherence criterion can be applied to contextualized biomarker data so that a biomarker data can be accepted depending on a comparison of the contextualized data regarding the documentation and related conditions that exists, or occur, during the collection of the specific biomarker. Adherence criterion can be akin to a sanity check for a given piece of information, or group of information. Preferably, the adherence criterion can be applied to group of data, or information, and can be rejected if the adherence criterion is not fulfilled. In particular, such rejected data are then not used for further calculations that provide a therapy recommendation. Mainly, the rejected data can only be used to assess the adherence and/or to automatically trigger at least one further action. For example, such a triggered action can prompt the user to follow a structured collection procedure, or a single requested action, so that the adherence criterion can be fulfilled.

The adherence criterion can be also applied to a single data point/information so that, for instance, a biomarker datum can be accepted depending on a comparison of the contextualized data regarding the documentation and related conditions that exists, or occur, during the collection of the specific biomarker. If the adherence criterion is applied only to a single data point, the adherence criteria can be construed as an "acceptance criterion."

The term "acceptance criterion," therefore, can include an adherence criterion applied to a single data point but can also include further criteria which can be applied to a single data point. A single data point/information can be then accepted depending on contextualized data and, in addition, depending on conditions and/or results of a measurement of that specific biomarker. For example, if a measurement error is detected, the biomarker reading can be rejected because the acceptance criterion cannot be fulfilled, e.g., due to an under-dose detection, or other measurement errors, which can occur and can be detected by the system. Moreover, other criteria which define a specific range in which a measured value can be located can be defined as an acceptance criterion of a single data point/information. The acceptance criterion can be applied to contextualized biomarker data so that a single data point/information can be accepted depending on contextualized data regarding the documentation and related conditions that exists, or occur, during the collection of the specific biomarker and a comparison (e.g., assessment) of these data with a defined value/information or defined range(s) of the value for contextualized data.

Moreover, the acceptance criterion can include additional criteria related to measurement errors and/or defined ranges of measured values as described above. As used herein, a biomarker, or event value, can be "acceptable" if the user follows the appropriate and recommended steps (i.e., adherence), and, in a preferred embodiment, the resulting data are within a predicted range. For example, before a sample is taken, the acceptance criteria can establish whether the steps leading up to taking of the sample were accomplished. For example, the processor in response to a request displays the question, "Have you been fasting for the last 8 hours?," wherein a "Yes" response received by the processor via the user interface meets the acceptance criterion for this step. In another example, after the sample is taken, the processor can assess the received data for reasonableness using other acceptance criterion(s). For example, based on prior data, a fasting bG sample should be between 120-180 mg/dl, but the received value was of 340 mg/dl, and thus fails such acceptance criteria since it is outside the predefined range for an acceptable value. In such an example, the processor could prompt for an additional sample. If the re-sampling fails too (i.e., not between 120-180 mg/dl), the assessment provided by the processor can be that the patient has not fasted, and, thus, the processor, as instructed by the acceptance criterion upon a failing of the re-sampling, can automatically extend the events in the schedule of events accordingly. In this specific example, the acceptance criterion can be based on an adherence criterion for a single data point (to be fasted) as a first acceptance criterion in combination with a predefined range of the blood glucose value which can be expected under that condition. Only if both criteria are fulfilled, the acceptance criterion overall can be met.

Furthermore, the acceptance criterion for a single data point/information can be derived from criteria which can be generated based on other data points/information. For example, if the adherence criterion of the whole collection procedure during which a single data point is measured or the adherence criteria of neighboring values is under a predefined threshold, the single data point cannot be accepted. In other words, the acceptance criterion of a single data point can include not only the adherence criterion for the measurement of the specific biomarker reading but also the adherence criterion of further biomarker readings or of the whole collection procedure. In addition, further criteria based on neighboring or related values of the specific single data point/information can be determined. For example, if a pattern recognition is applied to biomarker readings with similar contextualized data as related to the single data point/information, the single data point/information cannot then be acceptance if a reduced reliability is presumed based on the pattern recognition. For example, if a fasting blood glucose reading is detected as too high for the specific person under the conditions of the contextualized data in comparison to biomarker readings under similar conditions, it can be assumed that data were wrongly recorded even if, for example, a measurement error and/or an adherence event could not detected by the system itself. Consequently, the acceptance criterion can be defined by predetermined criteria, for example, by predetermined values but can be also defined dynamically based on data which can be generated during a collection procedure whereby specific criteria in particular values can be derived therefrom. The acceptance criterion, therefore, can be used to prove the reliability of a single data point/information so that only those values, which are significant and/or have a high reliability, can be utilized for further calculation. As a consequence, the acceptance criterion can ensure that a calculation of an insulin adjustment parameter can be based only on these values which fulfill predefined conditions that are essential for a correct insulin bolus calculation and that are accepted as values with a high reliability.

The term "data event request" can mean an inquiry for a collection of data at a single point in space-time defined by a special set of circumstances, for example, defined by time-related or not time-related events.

The term "decentralized disease status assessment" can mean a determination of the degree or extent of progression of a disease performed by using a biomarker measurement of interest to deliver a value without sending a sample to a laboratory for assessment.

The term "medical use case or question" can mean at least one or more of a procedure, situation, condition, and/or question providing an uncertainty about the factuality of existence of some medical facts, combined with a concept that is not yet verified but that if true would explain certain facts or phenomena. Medical use case or question can be already deposited and stored in the system so that the diabetic person can select between different medical use cases or questions. Alternatively, the medical use case or question can be defined by the diabetic person themselves.

The terms "focused", "structured", and "episodic" are used herein interchangeably with the term "testing" and can mean a predefined sequence in which to conduct the testing.

The terms "software" and "program" may be used interchangeably herein.

FIG. 1 shows a chronic care management system 10 for a diabetes patient(s) 12 and a clinician(s) 14 along with others 16 having an interest in the chronic care management of the patient 12. Patient 12, having dysglycemia, may include persons with a metabolic syndrome, pre-diabetes, type 1 diabetes, type 2 diabetes, and gestational diabetes. The others 16 with an interest in the patient's care may include family members, friends, support groups, and religious organizations all of which can influence the patient's conformance with therapy. The patient 12 may have access to a patient computer 18, such as a home computer, which can connect to a public network 50 (wired or wireless), such as the internet, cellular network, etc., and couple to a dongle, docking station, or device reader 22 for communicating with an external portable device, such as a portable collection device 24. An example of a device reader is shown in the manual "Accu-Chek® Smart Pix Device Reader Diabetic person's Manual" (2008) available from Roche Diagnostics.

The collection device 24 can be essentially any portable electronic device that can function as an acquisition mechanism for determining and storing digitally a biomarker value(s) according to a structured collection procedure, and which can function to run the structured collection procedure and the method of the present disclosure. Greater details regarding various illustrated embodiments of the structured collection procedure are provided hereafter in later sections. In a preferred embodiment, the collection device 24 can be a self-monitoring blood glucose meter 26 or a continuous glucose monitor 28. An example of a blood glucose meter is the Accu-Chek® Active meter, and the Accu-Chek® Aviva meter described in the booklet "Accu-Chek® Aviva Blood Glucose Meter Owner's Booklet (2007), portions of which are disclosed in U.S. Pat. No. 6,645,368 B1 entitled "Meter and method of using the meter for determining the concentration of a component of a fluid" assigned to Roche Diagnostics Operations, Inc., which is hereby incorporated by reference. An example of a continuous glucose monitor is shown in U.S. Pat. No. 7,389,133 "Method and device for continuous monitoring of the concentration of an analyte" (Jun. 17, 2008) assigned to Roche Diagnostics Operations, Inc., which is hereby incorporated by reference.

In addition to the collection device 24, the patient 12 can use a variety of products to manage his or her diabetes including: test strips 30 carried in a vial 32 for use in the collection device 24; software 34 which can operate on the patient computer 18, the collection device 24, a handheld computing device 36, such as a laptop computer, a personal digital assistant, and/or a mobile phone; and paper tools 38. Software 34 can be pre-loaded or provided either via a computer readable medium 40 or over the public network 50 and loaded for operation on the patient computer 18, the collection device 24, the clinician computer/office workstation 25, and the handheld computing device 36, if desired. In still other embodiments, the software 34 can also be integrated into the device reader 22 that is coupled to the computer (e.g., computers 18 or 25) for operation thereon, or accessed remotely through the public network 50, such as from a server 52.

The patient 12 can also use for certain diabetes therapies additional therapy devices 42 and other devices 44. Additionally, therapy devices 42 can include devices such as an ambulatory infusion pump 46, an insulin pen 48, and a lancing device 51. An example of an ambulatory insulin pump 46 include but not limited thereto the Accu-Chek® Spirit pump described in the manual "Accu-Chek® Spirit Insulin Pump System Pump Diabetic person Guide" (2007) available from Disetronic Medical Systems AG. The other devices 44 can be medical devices that provide patient data such as blood pressure, fitness devices that provide patient data such as exercise information, and elder care device that provide notification to care givers. The other devices 44 can be configured to communicate with each other according to standards planned by Continua® Health Alliance. These therapy devices can be separate or integrated into the collection devices and data processing devices described herein.

The clinicians 14 for diabetes are diverse and can include e.g., nurses, nurse practitioners, physicians, endocrinologists, and other such health care providers. The clinician 14 typically has access to a clinician computer 25, such as a clinician office computer, which can also be provided with the software 34. A healthcare record system 27, such as Microsoft® HealthVault™ and Google™ Health, may also be used by the patient 12 and the clinician 14 on computers 18, 25 to exchange information via the public network 50 or via other network means (LANs, WANs, VPNs, etc.), and to store information such as collection data from the collection device 24, handheld collection device 36, blood glucose monitor 28, etc. to an electronic medical record of the patient e.g., EMR 53 (FIG. 2A) which can be provided to and from computer 18, 25 and/or server 52.

Figure 2:
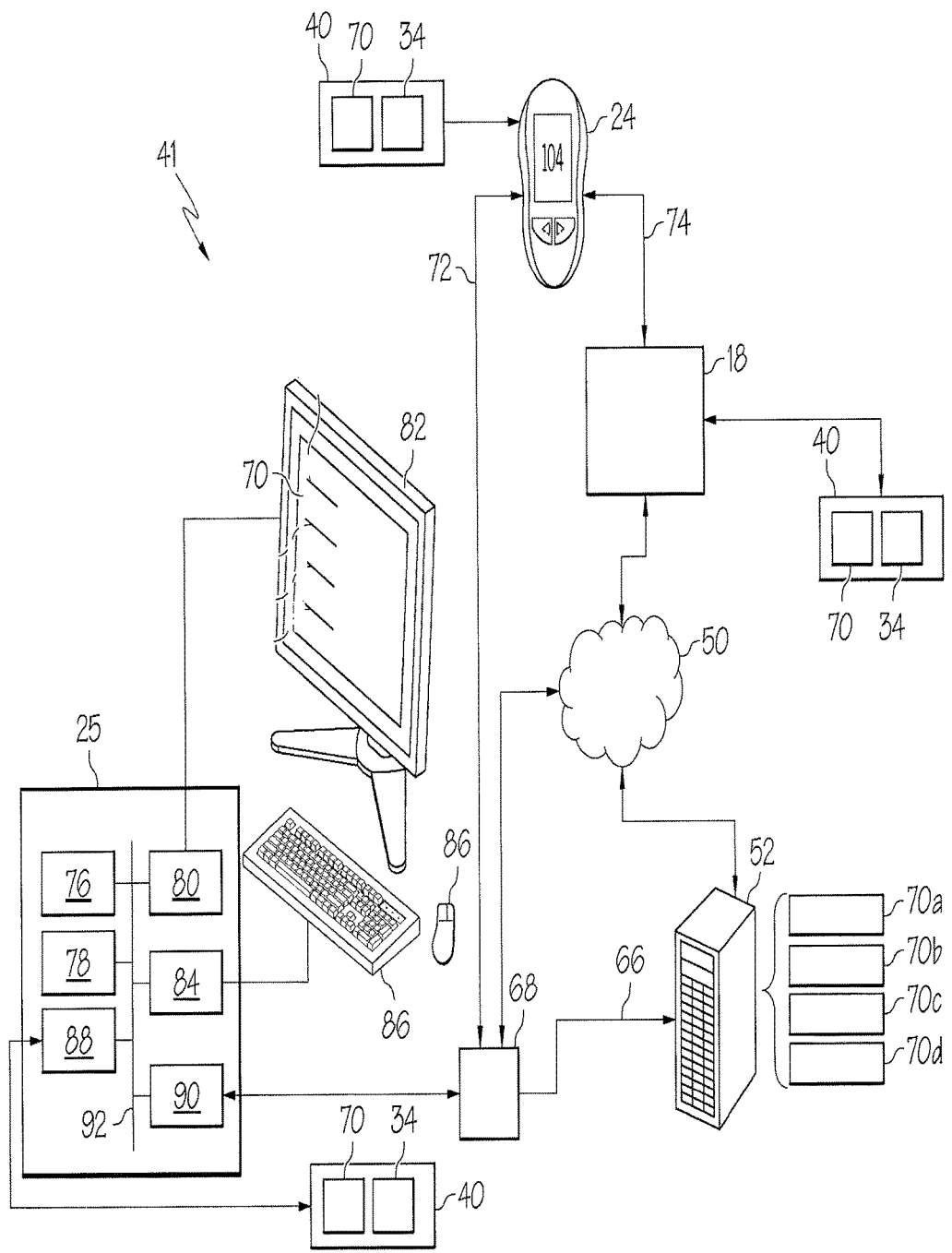
FIGS. 2 and 2A are diagrams showing embodiments of a system suitable for implementing a structured testing method according to an embodiment of the present disclosure.

Most patients 12 and clinicians 14 can interact over the public network 50 with each other and with others having computers/servers 52. Such others can include the patient's employer 54, a third party payer 56, such as an insurance company who pays some or all of the patient's healthcare expenses, a pharmacy 58 that dispenses certain diabetic consumable items, a hospital 60, a government agency 62, which can also be a payer, and companies 64 providing healthcare products and services for detection, prevention, diagnosis and treatment of diseases. The patient 12 can also grant permissions to access the patient's electronic health record to others, such as the employer 54, the payer 56, the pharmacy 58, the hospital 60, and the government agencies 62 via the healthcare record system 27, which can reside on the clinician computer 25 and/or one or more servers 52. Reference hereafter is also made to FIG. 2.

FIG. 2 shows a system embodiment suitable for implementing a structured testing method according to an embodiment of the present disclosure, which in another embodiment can be a part of the chronic care management system 10 and communicate with such components, via conventional wired or wireless communication means. The system 41 can include the clinician computer 25 that is in communication with a server 52 as well as the collection device 24. Communications between the clinician computer 25 and the server 52 can be facilitated via a communication link to the public network 50, to a private network 66, or combinations thereof. The private network 66 can be a local area network or a wide area network (wired or wireless) connecting to the public network 50 via a network device 68 such as a (web) server, router, modem, hub, and the likes.

In one embodiment, the server 52 can be a central repository for a plurality of structured collection procedures (or protocols) 70a, 70b, 70c, 70d (referred to in combination or collectively as one or more structured collection procedures 70), in which the details of a few exemplary structured collection procedures are provided in later sections. The server 52, as well as the network device 68, can function also as a data aggregator for completed ones of the structured collection procedures 70a, 70b, 70c, 70d. Accordingly, in such an embodiment, data of a completed collection procedure(s) from a collection device of the patient 12 can then be provided from the server 52 and/or network device 68 to the clinician computer 25 when requested in response to retrieval for such patient data.

Figure 2A:
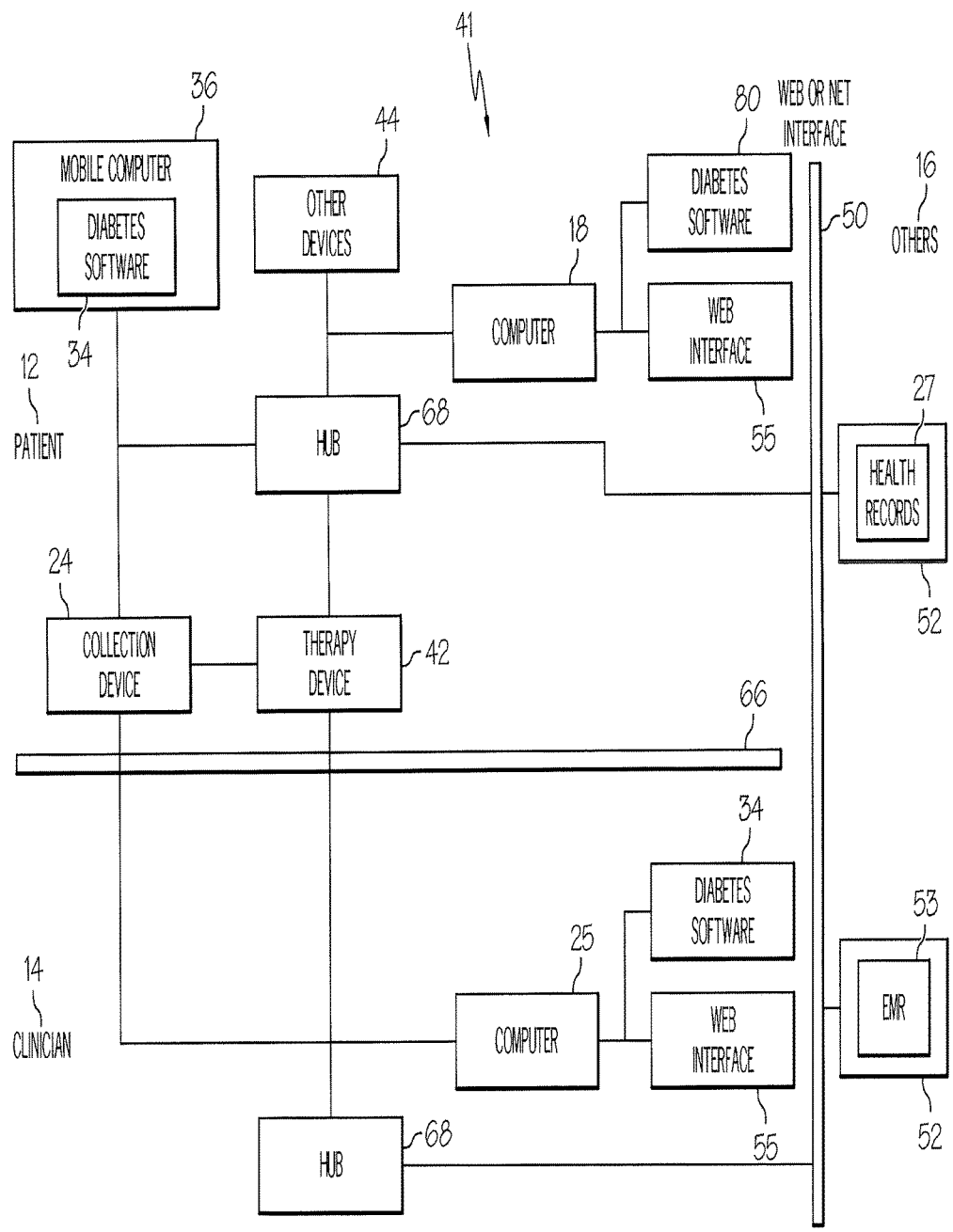

In one embodiment, one or more of the plurality of structured collection procedures 70a, 70b, 70c, 70d on the server 52 can be provided over the public network 50, such as through a secure web interface 55 (FIG. 2A, showing another embodiment of the system 41) implemented on the patient computer 18, the clinician computer 25, and/or the collection device 24. In another embodiment, the clinician computer 25 can serve as the interface (wired or wireless) 72 between the server 52 and the collection device 24. In still another embodiment, the structured collection procedures 70a, 70b, 70c, 70d, as well as software 34, may be provided on a computer readable medium 40 and loaded directed on the patient computer 18, the clinician computer 25, and/or the collection device 24. In still another embodiment, the structured collection procedures 70a, 70b, 70c, 70d may be provided pre-loaded (embedded) in memory of the collection device 24. In still other embodiments, new/updated/modified structured collection procedures 70a, 70b, 70c, 70d may be sent between the patient computer 18, the clinician computer 25, the server 52 and/or the collection device 24 via the public network 50, the private network 66, via a direct device connection (wired or wireless) 74, or combinations thereof. Accordingly, in one embodiment the external devices e.g., computer 18 and 25, can be used to establish a communication link 72, 74 between the collection device 24 and still further electronic devices such as other remote Personal Computer (PC), and/or servers such as through the public network 50, such as the Internet and/or other communication networks (e.g., LANs, WANs, VPNs, etc.), such as private network 66.

Figure 3:
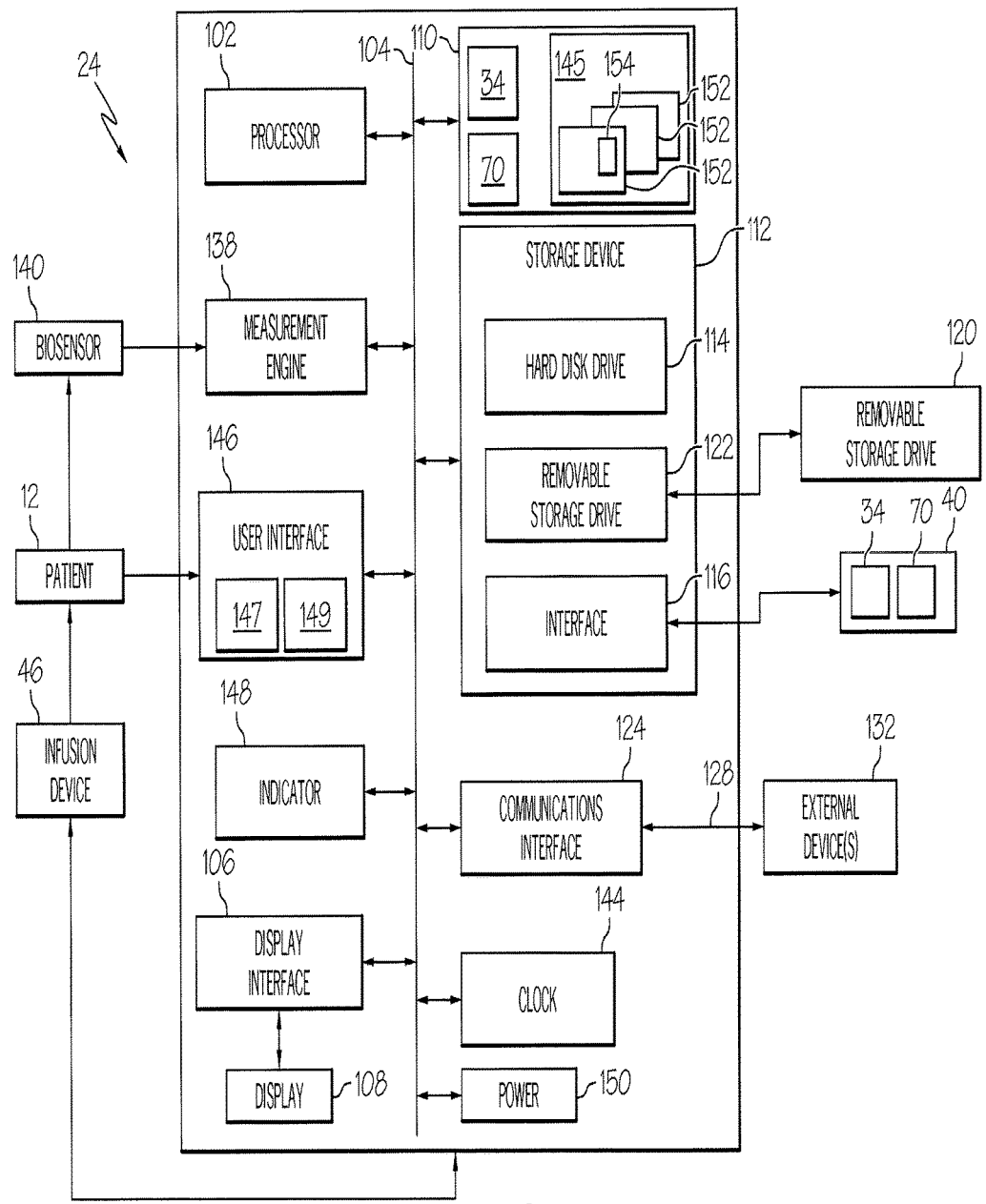
FIG. 3 shows a block diagram of a collection device embodiment according to the present disclosure.

The clinician computer 25, as a conventional personal computer/workstation, can include a processor 76 which executes programs, such as software 34, and such as from memory 78 and/or computer readable medium 40. Memory 78 can include system memory (RAM, ROM, EEPROM, etc.), and storage memory, such as hard drives and/or flash memory (internal or external). The clinician computer 25 can also include a display driver 80 to interface a display 82 with the processor 76, input/output connections 84 for connecting diabetic person interface devices 86, such as a keyboard and mouse (wired or wireless), and computer readable drives 88 for portable memory and discs, such as computer readable medium 40. The clinician computer 25 can further include communication interfaces 90 for connections to the public network 50 and other devices, such as collection device 24 (wired or wireless), and a bus interface 92 for connecting the above mentioned electronic components to the processor 76. Reference hereafter is now made to FIG. 3.

FIG. 3 is a block diagram conceptually illustrating the portable collection device 24 depicted in FIG. 2. In the illustrated embodiment, the collection device 24 can include one or more microprocessors, such as processor 102, which may be a central processing unit comprising at least one more single or multi-core and cache memory, which can be connected to a bus 104, which may include data, memory, control and/or address buses. The collection device 24 can include the software 34, which provides instruction codes that causes a processor 102 of the device to implement the methods of the present disclosure that are discussed hereafter in later sections. The collection device 24 may include a display interface 106 providing graphics, text, and other data from the bus 104 (or from a frame buffer not shown) for display on a display 108. The display interface 106 may be a display driver of an integrated graphics solution that utilizes a portion of main memory 110 of the collection device 24, such as random access memory (RAM) and processing from the processor 102 or may be a dedicated graphic processing unit. In another embodiment, the display interface 106 and display 108 can additionally provide a touch screen interface for providing data to the collection device 24 in a well-known manner.

Main memory 110 in one embodiment can be random access memory (RAM), and in other embodiments may include other memory such as a ROM, PROM, EPROM or EEPROM, and combinations thereof. In one embodiment, the collection device 24 can include secondary memory 112, which may include, for example, a hard disk drive 114 and/or a computer readable medium drive 116 for the computer readable medium 40, representing for example, at least one of a floppy disk drive, a magnetic tape drive, an optical disk drive, a flash memory connector (e.g., USB connector, Firewire connector, PC card slot), etc. The drive 116 reads from and/or writes to the computer readable medium 40 in a well-known manner. Computer readable medium 40, represents a floppy disk, magnetic tape, optical disk (CD or DVD), flash drive, PC card, etc. which is read by and written to by the drive 116. As will be appreciated, the computer readable medium 40 can have stored therein the software 34 and/or structured collection procedures 70a, 70b, 70c, and 70d as well as data resulting from completed collections performed according to one or more of the collection procedures 70a, 70b, 70c, and 70d.

In alternative embodiments, secondary memory 112 may include other means for allowing the software 34, the collection procedures 70a, 70b, 70c, 70d, other computer programs or other instructions to be loaded into the collection device 24. Such means may include, for example, a removable storage unit 120 and an interface connector 122. Examples of such removable storage units/interfaces can include a program cartridge and cartridge interface, a removable memory chip (e.g., ROM, PROM, EPROM, EEPROM, etc.) and associated socket, and other removable storage units 120 (e.g. hard drives) and interface connector 122 which allow software and data to be transferred from the removable storage unit 120 to the collection device 24.

The collection device 24 in one embodiment can include a communication module 124. The communication module 124 allows software (e.g., the software 34, the collection procedures 70a, 70b, 70c, and 70d) and data (e.g., data resulting from completed collections performed according to one or more of the collection procedures 70a, 70b, 70c, and 70d) to be transferred between the collection device 24 and an external device(s) 126. Examples of communication module 124 may include one or more of a modem, a network interface (such as an Ethernet card), a communications port (e.g., USB, Firewire, serial, parallel, etc.), a PC or PCMCIA slot and card, a wireless transceiver, and combinations thereof. The external device(s) 126 can be the patient computer 18, the clinician computer 25, the handheld computing devices 36, such as a laptop computer, a personal digital assistance (PDA), a mobile (cellular) phone, and/or a dongle, a docking station, or device reader 22. In such an embodiment, the external device 126 may provided and/or connect to one or more of a modem, a network interface (such as an Ethernet card), a communications port (e.g., USB, Firewire, serial, parallel, etc.), a PCMCIA slot and card, a wireless transceiver, and combinations thereof for providing communication over the public network 50 or private network 66, such as with the clinician computer 25 or server 52. Software and data transferred via communication module 124 can be in the form of wired or wireless signals 128, which may be electronic, electromagnetic, optical, or other signals capable of being sent and received by communication module 124. For example, as is known, signals 128 may be sent between communication module 124 and the external device(s) 126 using wire or cable, fiber optics, a phone line, a cellular phone link, an RF link, an infrared link, other communications channels, and combinations thereof. Specific techniques for connecting electronic devices through wired and/or wireless connections (e.g. USB and Bluetooth, respectively) are well known in the art.

In another embodiment, the collection device 24 can be used with the external device 132, such as provided as a handheld computer or a mobile phone, to perform actions such as prompt a patient to take an action, acquire a data event, and perform calculations on information. An example of a collection device combined with such an external device 126 provided as a hand held computer is disclosed in U.S. patent application Ser. No. 11/424,757 filed Jun. 16, 2006 entitled "System and method for collecting patient information from which diabetes therapy may be determined," assigned to Roche Diagnostics Operations, Inc., which is hereby incorporated by reference. Another example of a handheld computer is shown in the diabetic person guide entitled "Accu-Chek® Pocket Compass Software with Bolus Calculator Diabetic person Guide" (2007) available from Roche Diagnostics.

In the illustrative embodiment, the collection device 24 can provide a measurement engine 138 for reading a biosensor 140. The biosensor 140, which in one embodiment is the disposable test strip 30 (FIG. 1), is used with the collection device 24 to receive a sample such as for example, of capillary blood, which is exposed to an enzymatic reaction and measured by electrochemistry techniques, optical techniques, or both by the measurement engine 138 to measure and provide a biomarker value, such as for example, a blood glucose level. An example of a disposable test strip and measurement engine is disclosed in U.S. Patent Pub. No. 2005/0016844 A1 "Reagent stripe for test strip" (Jan. 27, 2005), and assigned to Roche Diagnostics Operations, Inc., which is hereby incorporated by reference. In other embodiments, the measurement engine 138 and biosensor 140 can be of a type used to provide a biomarker value for other types of sampled fluids or analytes besides or in addition to glucose, heart rate, blood pressure measurement, and combinations thereof. Such an alternative embodiment is useful in embodiments where values from more than one biomarker type are requested by a structured collection procedure according to the present disclosure. In still another embodiment, the biosensor 140 may be a sensor with an indwelling catheter(s) or being a subcutaneous tissue fluid sampling device(s), such as when the collection device 24 is implemented as a continuous glucose monitor (CGM) in communication with an infusion device, such as pump 46 (FIG. 1). In still another embodiments, the collection device 24 can be a controller implementing the software 34 and communicating between the infusion device (e.g., ambulatory infusion pump 46 and electronic insulin pen 48) and the biosensor 140.

Data, comprising at least the information collected by the biosensor 140, is provided by the measurement engine 138 to the processor 102 which may execute a computer program stored in memory 110 to perform various calculations and processes using the data. For example, such a computer program is described by U.S. patent application Ser. No. 12/492,667, filed Jun. 26, 2009, titled "Method, System, and Computer Program Product for Providing Both an Estimated True Mean Blood Glucose Value and Estimated Glycated Hemoglobin (HbA1C) Value from Structured Spot Measurements Of Blood Glucose," and assigned to Roche Diagnostics Operations, Inc., which is hereby incorporated by reference. The data from the measurement engine 138 and the results of the calculation and processes by the processor 102 using the data is herein referred to as self-monitored data. The self-monitored data may include, but not limited thereto, the glucose values of a patient 12, the insulin dose values, the insulin types, and the parameter values used by processor 102 to calculate future glucose values, supplemental insulin doses, and carbohydrate supplement amounts as well as such values, doses, and amounts. Such data along with a date-time stamp 169 for each measured glucose value and administered insulin dose value is stored in a data file 145 of memory 110 and/or 112. An internal clock 144 of the collection device 24 can supply the current date and time to processor 102 for such use.

The collection device 24 can further provide a diabetic person interface 146, such as buttons, keys, a trackball, touchpad, touch screen, etc. for data entry, program control and navigation of selections, choices and data, making information requests, and the likes. In one embodiment, the diabetic person interface 146 can comprises one or more buttons 147, 149 for entry and navigation of the data provided in memory 110 and/or 112. In one embodiment, the diabetic person can use one or more of buttons 147, 149 to enter (document) contextualizing information, such as data related to the everyday lifestyle of the patient 12 and to acknowledge that prescribed tasks are completed. Such lifestyle data may relate to food intake, medication use, energy levels, exercise, sleep, general health conditions and overall well-being sense of the patient 12 (e.g., happy, sad, rested, stressed, tired, etc.). Such lifestyle data can be recorded into memory 110 and/or 112 of the collection device 24 as part of the self-monitored data via navigating through a selection menu displayed on display 108 using buttons 147, 149 and/or via a touch screen diabetic person interface provided by the display 108. It is to be appreciated that the diabetic person interface 146 can also be used to display on the display 108 the self monitored data or portions thereof, such as used by the processor 102 to display measured glucose levels as well as any entered data.

In one embodiment, the collection device 24 can be switched on by pressing any one of the buttons 147, 149 or any combination thereof. In another embodiment, in which the biosensor 140 is a test-strip, the collection device 24 can be automatically switched on when the test-strip is inserted into the collection device 24 for measurement by the measurement engine 138 of a glucose level in a sample of blood placed on the test-strip. In one embodiment, the collection device 24 can be switched off by holding down one of the buttons 147, 149 for a pre-defined period of time, or in another embodiment can be shut down automatically after a pre-defined period of non-use of the diabetic person interface 146.

An indicator 148 can also be connected to processor 102, and which can operate under the control of processor 102 to emit audible, tactile (vibrations), and/or visual alerts/reminders to the patient of daily times for bG measurements and events, such as for example, to take a meal, of possible future hypoglycemia, and the likes. A suitable power supply 150 is also provided to power the collection device 24 as is well known to make the device portable.

As mentioned above previously, the collection device 24 may be pre-loaded with the software 34 or by provided therewith via the computer readable medium 40 as well as received via the communication module 124 by signal 128 directly or indirectly though the external device 132 and/or network 50. When provided in the latter matter, the software 34 when received by the processor 102 of the collection device 24 is stored in main memory 110 (as illustrated) and/or secondary memory 112. The software 34 contains instructions, when executed by the processor 102, enables the processor to perform the features/functions of the present disclosure as discussed herein in later sections. In another embodiment, the software 34 may be stored in the computer readable medium 40 and loaded by the processor 102 into cache memory to cause the processor 102 to perform the features/functions of the disclosure as described herein. In another embodiment, the software 34 is implemented primarily in hardware logic using, for example, hardware components such as application specific integrated circuits (ASICs). Implementation of the hardware state machine to perform the feature/functions described herein will be apparent to persons skilled in the relevant art(s). In yet another embodiment, the disclosure is implemented using a combination of both hardware and software.

In an example software embodiment of the disclosure, the methods described hereafter can be implemented in the C++ programming language, but could be implemented in other programs such as, but not limited to, Visual Basic, C, C#, Java or other programs available to those skilled in the art. In still other embodiment, the program 34 may be implemented using a script language or other proprietary interpretable language used in conjunction with an interpreter. Reference hereafter is also made to FIG. 4.

FIG. 4 depicts in tabular form a data file 145 containing data records 152 of self-monitored data 154 resulting from a structured collection procedure according to an embodiment of the present disclosure. The data records 152 (e.g., rows) along with the self-monitoring data 154 (e.g., various one of the columns) can also provide associated therewith contextual information 156 (e.g., other various ones of the columns as well as via row and column header information). Such contextual information 156 can be collected either automatically, such as for example via input received automatically from the measurement engine, the biosensor, and/or any one of the other devices, or via input received from the diabetic person interface which was manually entered by the patient in response to a collection request (e.g., a question displayed by the processor 102 on the display 108) during the structured collection procedure. Accordingly, as such contextual information 156 can be provided with each data record 152 in a preferred embodiment, such information is readily available to a physician and no further collection of such information is necessarily needed to be provided again by the patient either manually or orally after completing the structured collection procedure. In another embodiment, if such contextual information 156 and/or additional contextual information is collected after completion of a structured collection procedure according to the present disclosure, such information may be provided in the associated data file and/or record 145, 152 at a later time such as via one of the computers 18, 25. Such information would then be associated with the self-monitored data in the data file 145, and thus would not need to be provided again orally or manually. Such a process in the latter embodiment may be needed in the situation where the structured collection procedure is implemented as or partly as a paper tool 38 which is used with a collection device incapable of running the software 34 implementing such a structured collection procedure.

It is to be appreciated that the date file 145 (or portions thereof, such as only the self-monitored data 154) can be sent/downloaded (wired or wireless) from the collection device 24 via the communication module 124 to another electronic device, such the external device 132 (PC, PDA, or cellular telephone), or via the network 50 to the clinician computer 25. Clinicians can use diabetes software provided on the clinician computer 25 to evaluate the received self-monitored data 154 as well as the contextual information 156 of the patient 12 for therapy results. An example of some of the functions which may be incorporated into the diabetes software and which is configured for a personal computer is the Accu-Chek® 360 Diabetes Management System available from Roche Diagnostics that is disclosed in U.S. patent application Ser. No. 11/999,968 filed Dec. 7, 2007, titled "METHOD AND SYSTEM FOR SETTING TIME BLOCK," and assigned to Roche Diagnostics Operations, Inc., which is hereby incorporated by reference.

In a preferred embodiment, the collection device 24 can be provided as portable blood glucose meter, which is used by the patient 12 for recording self-monitored data comprising insulin dosage readings and spot measured glucose levels. Examples of such bG meters as mentioned above previously include but are not limited to, the Accu-Chek® Active meter and the Accu-Chek® Aviva system both by Roche Diagnostics, Inc. which are compatible with the Accu-Chek® 360° Diabetes management software to download test results to a personal computer or the Accu-Chek® Pocket Compass Software for downloading and communication with a PDA. Accordingly, it is to be appreciated that the collection device 24 can include the software and hardware necessary to process, analyze and interpret the self monitored data in accordance with predefined flow sequences (as described below in detail) and generate an appropriate data interpretation output. In one embodiment, the results of the data analysis and interpretation performed upon the stored patient data by the collection device 24 can be displayed in the form of a report, trend-monitoring graphs, and charts to help patients manage their physiological condition and support patient-doctor communications. In other embodiments, the bG data from the collection device 24 may be used to generated reports (hardcopy or electronic) via the external device 132 and/or the patient computer 18 and/or the clinician computer 25.

The collection device 24 can further provide the diabetic person and/or his or her clinician with at least one or more of the possibilities comprising: a) editing data descriptions, e.g. the title and description of a record; b) saving records at a specified location, in particular in diabetic person-definable directories as described above; c) recalling records for display; d) searching records according to different criteria (date, time, title, description etc.); e) sorting records according to different criteria (e.g., values of the bG level, date, time, duration, title, description, etc.); f) deleting records; g) exporting records; and/or h) performing data comparisons, modifying records, excluding records as is well known.

As used herein, lifestyle can be described in general as a pattern in an individual's habits such as meals, exercise, and work schedule. The individual additionally may be on medications such as insulin therapy or orals that they are required to take in a periodic fashion. Influence of such action on glucose is implicitly considered by the present disclosure.

It is to be appreciated that the processor 102 of the collection device 24 can implement one or more structured collection procedures 70 provided in memory 110 and/or 112. Each structured collection procedure 70 in one embodiment can be stand-alone software, thereby providing the necessary program instructions which when executed by the processor 102 causes the processor to perform the structure collection procedure 70 as well as other prescribed functions. In other embodiments, each structured collection procedure 70 can be part of the software 34, and can be then be selectively executed by the processor 102 either via receiving a selection from a menu list provided in the display 108 from the diabetic person interface 146 in one embodiment or via activation of a particular diabetic person interface, such as a structured collection procedure run mode button (not shown) provided to the collection device 24 in another embodiment. It is to be appreciated that the software 34, likewise, provides the necessary program instructions which when executed by the processor 102 causes the processor to perform the structure collection procedure 70 as well as other prescribed functions of the software 34 discussed herein. One suitable example of having a selectable structured collection procedure provided as a selectable mode of a collection meter is disclosed by in U.S. patent application Ser. No. 12/491,523, filed Jun. 25, 2009, titled "Episodic Blood Glucose Monitoring System With An Interactive Graphical Diabetic person Interface And Methods Thereof," assigned to Roche Diagnostics Operations, Inc., which is hereby incorporated by reference.

In still another embodiment, a command instruction can be sent from the clinician computer 25 and received by the processor 102 via the communication module 124, which places the collection device 24 in a collection mode which runs automatically the structured collection procedure 70. Such a command instruction may specify which of the one or more structured collection procedures to run and/or provide a structured collection procedure to run. In still another embodiment, a list of defined medical use cases or medical questions can be presented on the display 108 by the processor 102, and a particular structured collection procedure 70 can be automatically chosen by the processor 102 from a plurality of structured collection procedures (e.g., procedures 70a, 70b, 70c, and 70d) depending on the selection of the defined medical use cases or medical questions received by the processor 102 via the diabetic person interface 146.

In still another embodiment, after selection, the structured collection procedure(s) 70 can be provided through the computer readable medium e.g., 40 and loaded by the collection device 24, downloaded from computer 18 or 25, the other device(s) 132, or server 52. Server 52, for example, may be a healthcare provider or company providing such pre-defined structured collection procedures 70 for downloading according to a selected defined medical use case or question. It is to be appreciated that the structured collection procedure(s) 70 may be developed by a healthcare company (e.g. company 64) and implemented via the public network 50 through a webpage and/or made available for downloading on server 52, such as illustrated in FIG. 2. In still other embodiments, notices that a new structured collection procedure 70 is available for use on the collection device 24 to help address a particular use case/medical question that a diabetic person (e.g., healthcare provider and patient) may have can be provided in any standard fashion, such for via postal letters/cards, email, text messaging, tweets, and the likes.

In some embodiments, as mentioned above previously, a paper tool 38 can perform some of the functions provided by the diabetes software 34. An example of some of the functions which may be incorporated into the diabetes software 34 and which is configured as a paper tool 38 is the Accu-Chek® 360 View Blood Glucose Analysis System paper form available from Roche Diagnostics also disclosed in U.S. patent application Ser. No. 12/040,458 filed Feb. 29, 2007 entitled "Device and method for assessing blood glucose control," assigned to Roche Diagnostic Operations, Inc., which is hereby incorporated by reference.

In still another embodiment, the software 34 can be implemented on the continuous glucose monitor 28 (FIG. 1). In this manner, the continuous glucose monitor 28 can be used to obtain time-resolved data. Such time-resolved data can be useful to identify fluctuations and trends that would otherwise go unnoticed with spot monitoring of blood glucose levels and standard HbA1c tests. Such as, for example, low overnight glucose levels, high blood glucose levels between meals, and early morning spikes in blood glucose levels as well as how diet and physical activity affect blood glucose along with the effect of therapy changes.

In addition to collection device 24 and software 34, clinicians 14 can prescribe other diabetes therapy devices for patients 12 such as an ambulatory insulin pump 46 as well as electronically based insulin pen 48 (FIG. 1). The insulin pump 46 typically includes configuration software such as that disclosed in the manual "Accu-Chek® Insulin Pump Configuration Software" also available from Disetronic Medical Systems AG. The insulin pump 46 can record and provide insulin dosage and other information, as well as the electronically based insulin pen 48, to a computer, and thus can be used as another means for providing biomarker data as requested by the structured collection procedure 70 (FIG. 2) according to the present disclosure.

It is to be appreciated that, and as mentioned above previously, one or more of the method steps discussed hereafter can be configured as a paper tool 38 (FIG. 1), but preferably all the method steps are facilitated electronically on system 41 (FIG. 2) or on any electronic device/computer, such as collection device 24, having a processor and memory as a program(s) residing in memory. As is known, when a computer executes the program, instructions codes of the program cause the processor of the computer to perform the method steps associated therewith. In still other embodiments, some or all of the method steps discussed hereafter can be configured on computer readable medium 40 storing instruction codes of a program that, when executed by a computer, cause the processor of the computer to perform the method steps associated therewith. These method steps are now discussed in greater detail hereafter with reference made to FIG. 5A.

Testing Method Embodiments for Optimizing the Titration of Insulin

Figure 5A:
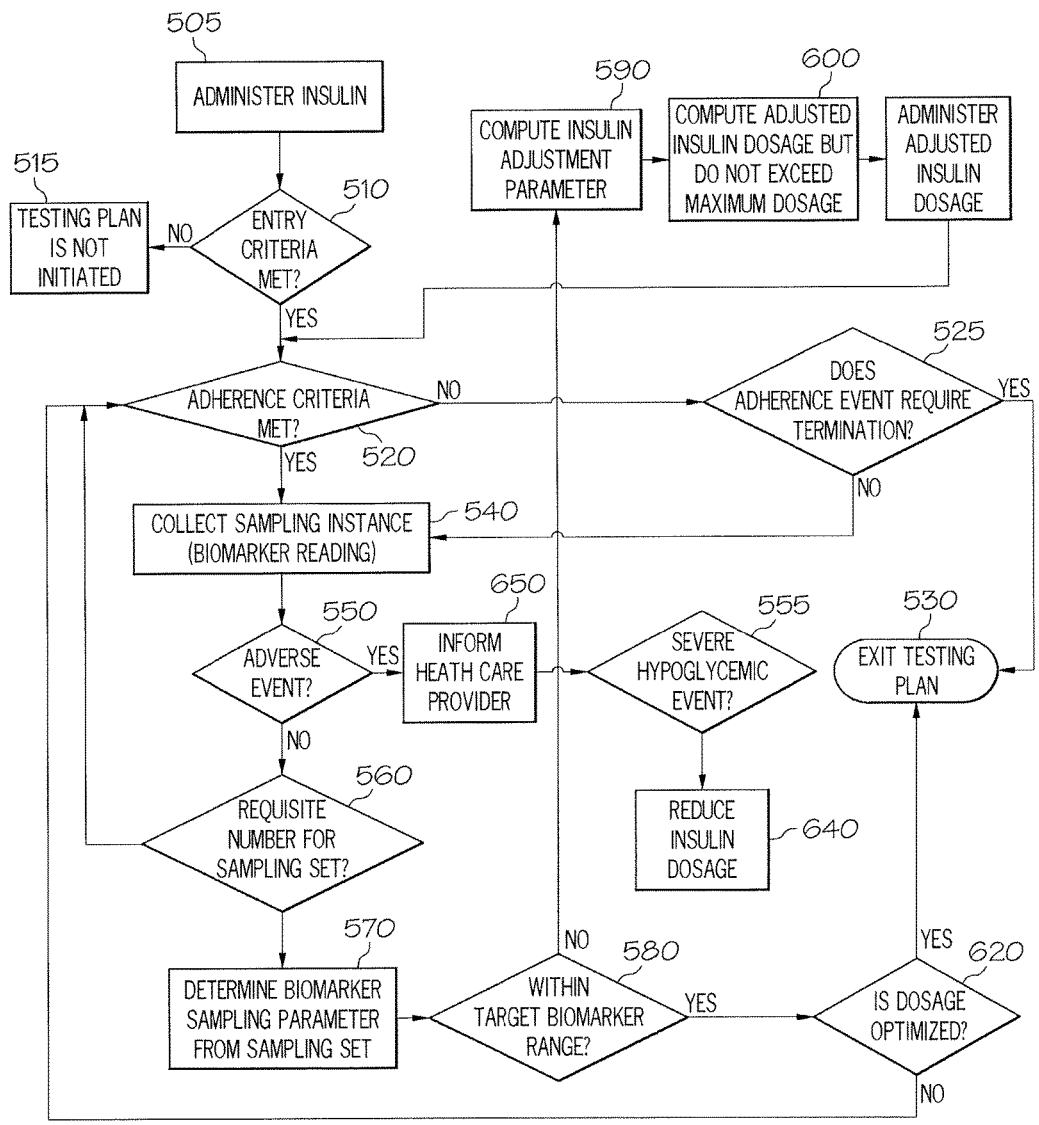
FIGS. 5A-5D shows flow charts depicting testing methods for optimizing the titration of insulin according to embodiments of the present disclosure.

FIG. 5A provides an exemplary embodiment of testing methods for optimizing the titration of insulin dosage, which thereby yield dosages of insulin which maintain biomarker levels within a desired range. In one embodiment, the titrated insulin may be basal insulin. Upon starting the testing method, the dosage of insulin is typically the initial prescribed dosage, for example, the initial prescribed dosage listed on the package. However, other dosages are contemplated depending on what stage of the testing method, as the entry criteria may be considered before every biomarker reading. Consequently, the initial dosage may be an adjusted dosage above the initial prescribed dosage, the maximum allowable dosage, or even the optimized dosage. It is contemplated that the testing method may be used to obtain the optimized insulin value, or may be used post-optimization to verify that the insulin dosage is still optimal.

Figure 5B:
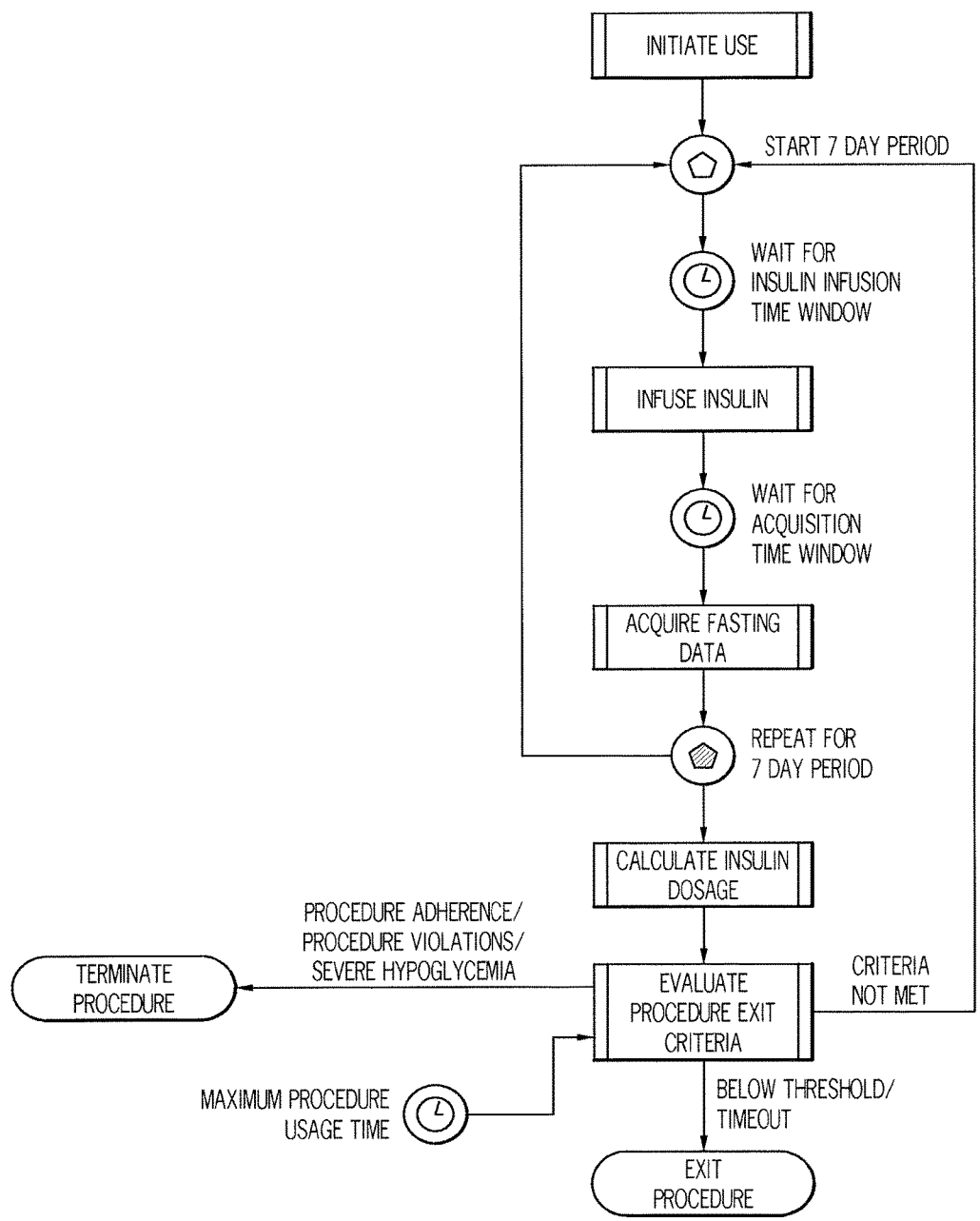
Figure 5C:
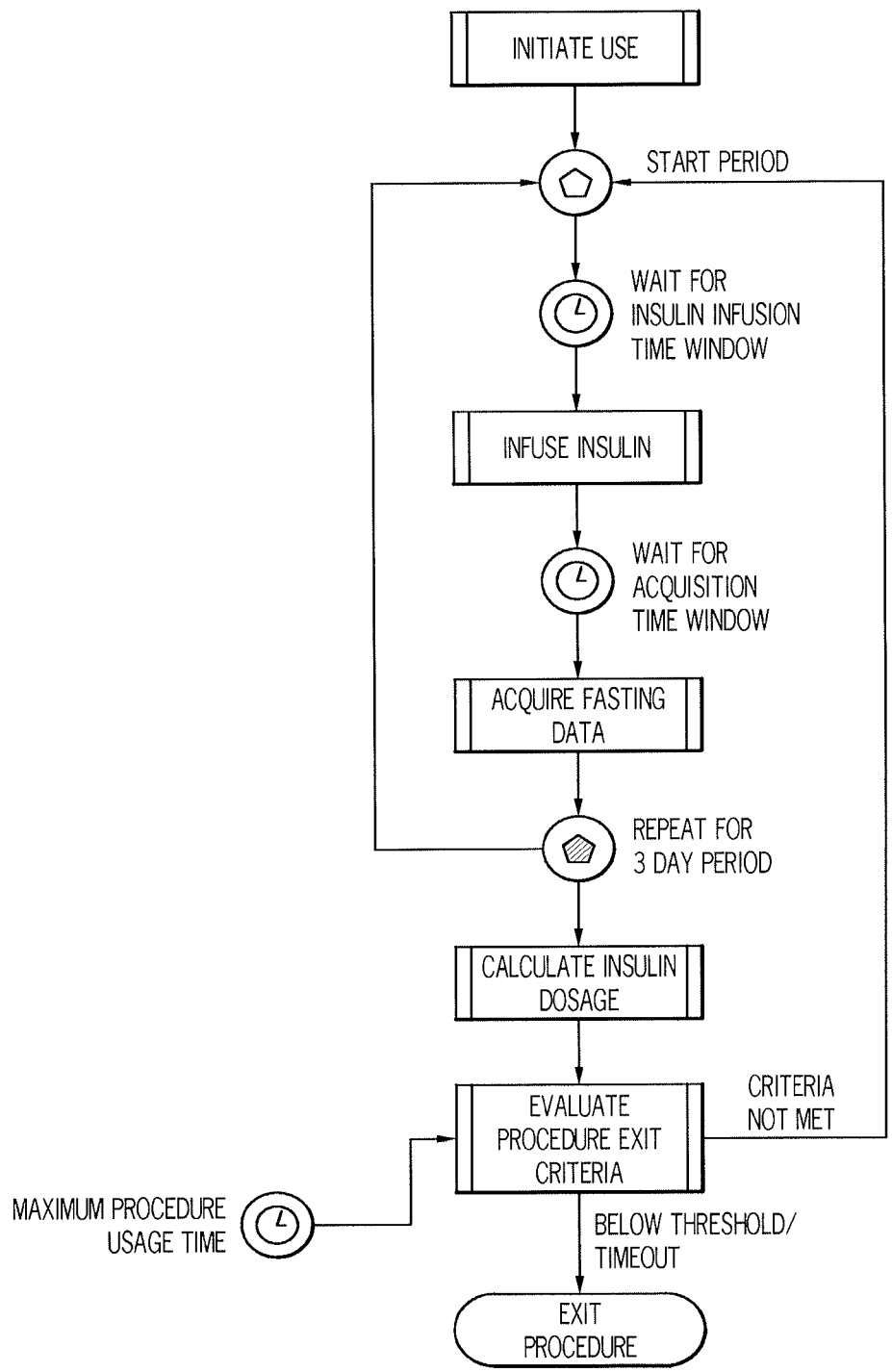
Figure 5D:
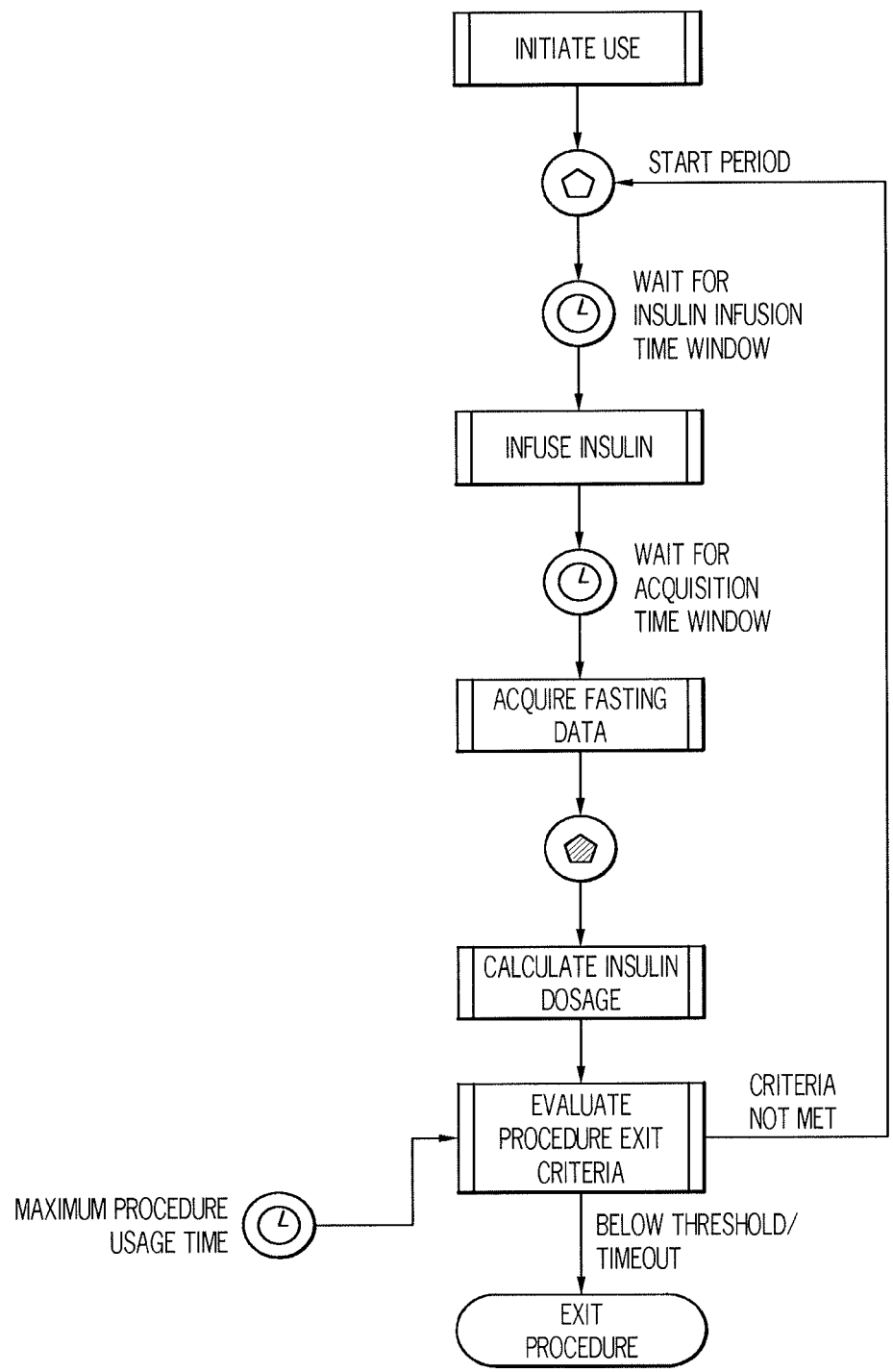

In the embodiments of FIG. 5A, the testing methods may optionally require the consideration of entry criteria 510 before beginning collection of the biomarker data. It is contemplated that the diabetic person, the healthcare provider, or both may determine whether the entry criteria are met. The entry criteria, which in some embodiments may be established by the healthcare provider, may relate to the age, weight, and medical history of the diabetic person. Consequently, the testing method may require a diabetic person to receive a check-up or physical to ensure the diabetic person satisfies the entry criteria. For instance, the entry criteria may specify the fasting plasma glucose (FPG) level or glycolated hemoglobin level as determined by the HbA1c test. The normal range for the HbA1c test is between 4-6% for people without diabetes, so the entry criteria may require values above about 6%, or in exemplary embodiment, between about 7.5% to about 10%. As an additional example of entry criteria, a fasting plasma glucose level of at least about 140 mg/dl is required. The entry criteria may also set requirements on weight or Body Mass Index (BMI). For example, the required BMI may be greater than about 25 kg/m2, or between about 26 kg/m2 to about 40 kg/m2. Additionally, the entry criteria may specify a desired age range (e.g., 30-70) or the number of years afflicted with diabetes (e.g., at least 2 years). Moreover, while it is contemplated that the testing method is applicable to persons afflicted all types of diabetes, the entry criteria may limit the testing method to type 2 diabetics. Furthermore, the entry criteria may center on the current diabetes treatment regimen of the diabetic person. For example, the entry criteria may require that the treatment regimen for the diabetic person be limited to oral anti-diabetes medication i.e., no injected insulin. Additionally, the entry criteria may require that the diabetic person not be ill or under stress. As stated above, while the embodiments of FIG. 5A are directed to the consideration of entry criteria, the present testing methods do not require the consideration of entry criteria before collection of biomarker data. For example, referring to the additional embodiments of FIGS. 5B-D, the embodiment of FIG. 5B requires the consideration of entry criteria; however, the embodiments of FIGS. 5C and 5D do not include such constraints.

Referring again to FIG. 5A, if the entry criteria are not met, the testing method will not be initiated 515. The diabetic person or healthcare provider may determine whether the entry criteria have been met, or the data processor may determine whether criteria have been met. If the entry criteria are met 510, then the diabetic person may commence with the testing method. However, in some embodiments, it may be required for the diabetic person satisfy adherence criteria 520 before the collection of biomarkers or the administration of insulin.

The adherence criteria 520 are the procedural requirements that the diabetic person must follow when conducting the testing method. To get a proper baseline for the biomarker readings, it may be beneficial to ensure all readings are taken uniformly, i.e., at approximately the same time of day for each sampling instance. Consequently, the adherence criteria 520 may specify that biomarker collection or insulin administration be conducted at the same time each day. To aid the diabetic person in satisfying the adherence criteria 520, the data processor display prompt the diabetic patient with audio and/or visual reminders to collect their biomarker sample, and enable the diabetic patient to set future reminders. In specific embodiments, the adherence criteria 520 may also require that the diabetic person fast for a set period of time prior to collecting the biomarker reading. The adherence criteria 520 may also be directed to determining whether the diabetic person is taking the correct dosage of insulin. In additional embodiments, the adherence criteria 520 may also require no recent hypoglycemic events or severe hypoglycemic events (low blood glucose events) a set period (e.g. one week) before the collection of biomarker data. Furthermore, the adherence criteria 520 may specify an exercise regimen or eating regimen for the diabetic person. As used herein, "eating regimen" means the typical eating regimen of the diabetic person in terms of calories, carbohydrate intake and protein intake.

If the diabetic person fails to meet any or all of the adherence criteria 520, the diabetic person may be informed, for example, by the display of the blood glucose meter that they failed to meet the adherence criterion. If the diabetic person fails to meet the adherence criteria 520, the data processor device may tag the adherence event or the diabetic person may record the occurrence of the adherence event. After the adherence event is recorded, the testing method is typically continued. However, if too many adherence events are recorded (e.g., more than 4 within a sample period, more than 20 adherence events within the entirety of execution), then the testing method may be terminated 525. Furthermore, the testing method may also evaluate adherence events differently. For example, there may be a tiered adherence event assessment, wherein adherence events are weighted. In one or more embodiments, if the adherence event does not impact the biomarker data, then it is not weighted as heavily as an adherence event that affects the biomarker data. For example, when a diabetic person fasts the requisite time period before taking a fasting blood glucose reading, but fails to record that the reading is a fasting blood glucose reading, this would be categorized diabetic as a less significant and thereby lower weighted adherence event, because the recording error does not affect the fasting blood glucose reading. In contrast, fasting less than the requisite period will impact the fasting blood glucose reading, and thus constitutes a more significant and thereby higher weighted adherence event.

If there is a violation event (e.g., a missed insulin administration), the testing method is more likely to be terminated than for an adherence event (e.g., fasting less than the required fasting period), because a violation event impacts the testing method more significantly. Since the present testing method is directed to optimizing insulin administration, it stands to reason that missing an insulin dose would be a significant violation event.

Like other instructions provided to the diabetic person throughout the testing method, the entry criteria or the adherence criteria 520 may be provided to the diabetic person via a paper instruction form, or a display unit on a data processing device or processor 102 as shown in FIG. 3. The data processing devices may be any electronic device described above. In one or more embodiments, the data processing device may be a computer or a blood glucose meter with a data processor and memory units therein. In addition to listing the entry criteria, adherence criteria 520, or both, the data processing device may prompt the diabetic person to answer medical questions, wherein the answers to the medical questions are used by the device to determine compliance with the entry criteria, or adherence criteria 520. The data processing device may inform the diabetic person of the failure to comply with the entry criteria or adherence criteria 520. For example, the data processing device may inform a diabetic person if subsequent sampling instances are not taken around the same time as the first sampling instance. The patient can record sampling instances or answer medical questions by entering the data event directly into a device or computer, wherein the processor 102 can store the information and provide additional analysis depending on the parameters of the testing method.

Referring again to FIG. 5A, the diabetic person may begin collection of one or more sampling sets of biomarker data. Each sampling set comprises a sufficient plurality of non-adverse sampling instances recorded over a collection period, which means at least two sampling instances which are not indicative of an adverse event e.g., a hypoglycemic or hyperglycemic event. Each sampling instance 540 comprises a biomarker reading at a single point in time. The collection period for the sampling set may be defined as multiple sampling instances within a day, multiple sampling instances within a week, multiple sampling instances within consecutive weeks, or multiple sampling instances on consecutive days within a week. The biomarker may relate to the levels of glucose, triglycerides, low density lipids, and high density lipids. In one exemplary embodiment, the biomarker reading is a blood glucose reading. In addition to the biomarker reading, each sampling instance may comprise the biomarker reading and other contextual data associated with the biomarker reading, wherein the contextual data is selected from the group consisting of the time of collection, the date of collection, the time when the last meal was consumed, affirmation that fasting has occurred for the requisite period, and combinations thereof. In the exemplary embodiment of FIG. 5B, the testing method occurs over a 7 day method which requires the diabetic patient to administer insulin 505 in the evening followed by the collection of fasting blood glucose reading the following morning. In addition to the morning biomarker collection, the diabetic patient may also be instructed to take an additional biomarker reading when the diabetic person is encountering the symptoms of hypoglycemia.

Referring again to FIG. 5A, upon collecting the biomarker reading, there is a determination as to whether the biomarker reading indicates an adverse event 550. While the present discussion of adverse events centers on hypoglycemic events and severe hypoglycemic events 555, which may necessitate medical assistance, it is contemplated that the adverse events may refer to undesirable levels of other biomarkers or medical indicators, e.g., lipids levels, blood pressure levels, etc. In one embodiment, this determination of adverse events may be performed by comparing the biomarker reading to a low threshold, for example, the hypoglycemic event or severe hypoglycemic event 555 thresholds shown in Table 1 below. If the biomarker reading is below one or both of these thresholds, then an adverse event may have occurred, and should be recorded as an adverse event, or specifically recorded as a hypoglycemic event or severe hypoglycemic event 555. As described above, this determination may be performed by a data processor unit, or may be entered manually by the diabetic person.

TABLE 1

| Blood Glucose Range (mg/dl) | Insulin Adjustment Parameter (units) |
| --- | --- |
| below 56 (severe hypoglycemic event) | −2 to −4 |
| 56-72 (hypoglycemic event) | 0 |
| 73 to 100 (target biomarker range) | 0 |
| 100-119 | +2 |
| 120-139 | +4 |
| 140-179 | +6 |
| 180 and above | +8 |

If there is an adverse event (e.g., a severe hypoglycemic event 555), in one embodiment, the instructions or data processing device may recommend that the diabetic person contacts their health care provider. In another embodiment, the system may automatically contact the health care provider (HCP). In addition, an adverse event may optionally lead to a dosage reduction. Referring to Table 1 above, if it is a hypoglycemic event (between 56-72 mg/dl), the HCP may be contacted 650, but the dosage is not adjusted (See FIG. 5). However, if it is a severe hypoglycemic event 555 (below 56 mg/dl), the dosage may be reduced by some amount (640), for example, 2 units, 4 units, or another amount as dictated by the low biomarker reading. In specific embodiments, if the recorded adverse event is a second measured severe hypoglycemic event 555 within the same day, the dosage is not reduced. In further embodiments, a data processing device may utilize an algorithm to automatically reduce the insulin dosage and instruct the diabetic person of the reduced insulin dosage. Moreover, the data processing device which collects the biomarker reading may automatically notify a healthcare provider of the adverse event, for example, by an automated email or text message.

If the biomarker reading is not adverse, the next step depends on whether or not the sampling set 560 has a sufficient number of non-adverse sampling instances. If only one sampling instance is required for the sampling set, then the biomarker sampling parameter may be calculated at that point; however, as stated above, the sampling set typically requires a plurality or at least two sampling instances for each sampling set. In exemplary embodiments, two or more sampling instances taken on consecutive days are required for each sampling set. If multiple sampling instances are required, then the diabetic person must continue to collect sampling instances.

Once the requisite number of sampling instances for the sampling set is obtained, the biomarker sampling parameter may be obtained 570. The biomarker sampling parameter may be determined by various algorithms or methodologies. For example, it may be determined by averaging sampling instances, summing the sampling instances, performing a graphical analysis on the sampling instances, performing a mathematical algorithm on the sampling set, or combinations thereof. In an exemplary embodiment, sampling instances (i.e., biomarker readings) are collected on at least three consecutive days, and the average of the three consecutive days is the biomarker sampling parameter.

After the biomarker sampling parameter is obtained, the value is compared to a target biomarker range 580. As used herein, the target biomarker range 580 means an acceptable range of biomarker in the diabetic person, which thereby demonstrates that the insulin is producing the desired physiological response. If the biomarker sampling parameter falls outside of the target biomarker range 580, then an insulin adjustment parameter may be calculated 590. The insulin adjustment parameter is associated with and computed from the biomarker sampling parameter. Various methodologies and algorithms are contemplated for calculating the insulin adjustment parameter. For example, the insulin adjustment parameter may be computed by locating the insulin adjustment parameter associated with the biomarker parameter in an insulin adjustment parameter lookup table (See Table 1 above). As shown above in the exemplary insulin adjustment parameter lookup table of Table 1, there may be multiple tiers which dictate how much the insulin dosage should be adjusted. For example, a fasting glucose level below 100 mg/dl but above 56 mg/dl will necessitate no adjustment to the insulin dosage. The greater the deviation from the target range, the higher the adjustment of insulin in units.

After determining the insulin adjustment parameter, the insulin dosage may be adjusted by the amount of the insulin adjustment parameter, as long as the insulin adjustment does not raise the insulin dosage above the maximum allowable dosage 600. The adjusted insulin dosage cannot exceed a maximum level set by the healthcare provider. Upon determining the adjusted insulin dosage value, the diabetic person may then be instructed to collect at least one additional sampling set at the adjusted insulin dosage per the above described collection procedures. The biomarker sampling parameter, the insulin adjustment parameter, and the adjusted insulin dosage may be computed manually by the diabetic person or via a data processing device.

If the biomarker sampling parameter is within a target biomarker range 580, there is no adjustment of the insulin dosage. Moreover, the insulin dosage may be considered optimized depending on other applicable criteria. Specifically, an insulin dosage may be considered optimized if one biomarker sampling parameter is within a target biomarker range, or it may be considered optimized if at least two consecutive biomarker sampling parameters are within a target biomarker range 620. If the optimization definition requires at least two consecutive biomarker sampling parameters within a target biomarker range, the diabetic person is then instructed to collect at least one additional sampling set at the adjusted insulin dosage per the above described collection procedures. After the insulin dosage is considered optimized, the diabetic person is instructed to exit the testing method. After exiting the testing method 530, the diabetic person may conduct further testing methods to determine the future efficacy of the optimized dosage.

In alternative embodiments, the diabetic patient may be instructed to exit the testing method 530 if the diabetic person has been undergoing the testing procedure for a long period, for example, 6 months or longer. Additionally, as described above, if there are multiple adherence or violation events, then the test may be automatically terminated by the data processing device or the diabetic patient may be instructed to exit the testing method.

Having described the disclosure in detail and by reference to specific embodiments thereof, it will be apparent that modifications and variations are possible without departing from the scope defined in the appended claims. More specifically, although some aspects of the present disclosure are identified herein as preferred or particularly advantageous, it is contemplated that the present disclosure is not necessarily limited to these preferred aspects of the disclosure.

All cited documents are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

The invention claimed is:

1. A testing method suitable for a diabetic person to optimize an administered insulin dosage comprising:
    providing a structured collection procedure from a server of a health care provider to a collection device configured to guide the diabetic person through the structured collection procedure and optimize the administered insulin dosage, wherein the collection device comprises a meter configured to measure one or more selected biomarkers, a processor disposed inside the meter and coupled to a memory, wherein the memory stores the structured collection procedure provided from the server, and software having instructions that when executed by the processor causes the processor to instruct the diabetic person to collect one or more sampling sets of biomarker data in accordance with the structured collection procedure, wherein the server is a central repository for a plurality of the structured collection procedures;
    executing the software on the collection device and according to instructions and timing provided by the structured collection procedure:
    collecting one or more sampling sets of biomarker data, wherein each of the one or more sampling sets comprises a plurality of sampling instances recorded over a collection period and each sampling instance of the plurality of sampling instances comprises an acceptable biomarker reading recorded upon compliance with one or more acceptance criterion based on at least one of a schedule-based action or a patient-based action and that is applied to the one or more sampling sets of biomarker data;
    wherein after each collection of the one or more sampling sets of biomarker data, said processor performs the processes of:
    calculating a biomarker sampling parameter from the one or more sampling sets of biomarker data and as a function of only these biomarker data that are in compliance with the one or more acceptance criterion;
    comparing the biomarker sampling parameter to a target biomarker range;
    calculating an insulin adjustment parameter associated with the biomarker sampling parameter in response to the biomarker sampling parameter falling outside the target biomarker range;
    adjusting an insulin dosage by an amount of the insulin adjustment parameter in response to the biomarker sampling parameter falling outside the target biomarker range and in response to the insulin dosage not exceeding maximum dosage; and
    exiting the testing method in response to the adjusted insulin dosage being optimized as an optimized insulin dosage such that the optimized insulin dosage is administered as the administered insulin dosage, otherwise repeating with a next sampling set of the one or more sampling sets of biomarker data, the optimized insulin dosage being achieved when the one or more biomarker sampling parameters fall within the target biomarker range.

2. The testing method of claim 1 wherein the insulin dosage is optimized when at least two consecutive biomarker sampling parameters fall within the target biomarker range.

3. The testing method of claim 1 further comprising conducting a new testing method after achieving the optimized insulin dosage.

4. The testing method of claim 1 wherein the collection period for the one or more sampling sets of biomarker data is defined as multiple sampling instances within a day, multiple sampling instances within a week, multiple sampling instances within consecutive weeks, or multiple sampling instances on consecutive days within a week.

5. The testing method of claim 1 wherein each sampling instance of the plurality of sampling instances comprises the acceptable biomarker reading and other contextual data associated with the acceptable biomarker reading, wherein the contextual data is selected from the group consisting of a time of collection, a date of collection, a time when the last meal was consumed, and combinations thereof.

6. The testing method of claim 1 further comprising collecting one or more additional sampling sets of biomarker data when the biomarker sampling parameter falls outside of the target biomarker range.

7. The testing method of claim 1 further comprising informing the health care provider of any biomarker readings indicative of an adverse event that is a hypoglycemic event.

8. The testing method of claim 1 wherein a biomarker reading below a lower threshold is indicative of an adverse event.

9. The testing method of claim 1 further comprising contacting the health care provider for any biomarker readings indicative of an adverse event.

10. The testing method of claim 1 wherein the administered insulin dosage is decreased for any biomarker readings indicative of an adverse event.

11. The testing method of claim 1 wherein the one or more acceptance criterion requires at least one of that a prescribed dosage be administered throughout the collection period and that a fasting period before collection of the one or more sampling sets of biomarker data.

12. The testing method of claim 1 further comprising meeting entry criteria required for beginning to collect the one or more sampling sets of biomarker data.

13. The testing method of claim 12 wherein the entry criteria requires at least one of that the diabetic person be afflicted with type 2 diabetes and that the diabetic person be limited to oral diabetes medication prior to conducting the testing method.

14. The testing method of claim 1 wherein the maximum insulin dosage is set by the health care provider.

15. The testing method of claim 1 wherein the biomarker sampling parameter is determined by at least one of averaging sampling instances, summing the sampling instances, performing a graphical analysis on the sampling instances, and performing a mathematical algorithm on the sampling set.

16. The testing method of claim 1 wherein the calculating of the insulin adjustment parameter comprises locating the insulin adjustment parameter associated with the biomarker parameter in an insulin adjustment parameter lookup table, utilizing an algorithm, and combinations thereof.

17. The testing method of claim 1 wherein the one or more acceptance criterion comprises one or more considerations selected from the group consisting of: a patient diet, fasting or eating regimen; a patient exercise regimen; a patient lifestyle; a patient sleep regimen; insulin dosage amounts; and timing of biomarker reading collection.

18. The testing method of claim 1 wherein the one or more acceptance criterion comprises an adherence criteria, and in response to the diabetic person failing to meet the adherence criteria, the processor tags the failing as an adherence event and informs the diabetic person via a display, then continues the testing method, wherein in response to a determination that a number of the adherence events in a sample period are obtained or a total number of the adherence events are reached in the testing method, the testing method is terminated.

19. The testing method of claim 18 wherein said processor performs the processes of categorizing, via the processor, the adherence events into tiers of either a lower weighted adherence event in response to a determination that the adherence event will not cause an error in at least one acceptable biomarker reading, or a higher weighted adherence event in response to a determination that the adherence event will cause the error in the at least one acceptable biomarker reading, wherein the lower weighted adherence event is an event that is not weighted as heavily as the higher weighted adherence event that affects the one or more sampling sets of biomarker data.

20. A testing method suitable for a diabetic person to optimize an administered insulin dosage comprising:
providing a structured collection procedure from a server of a health care provider to a collection device configured to guide the diabetic person through the structured collection procedure and optimize the administered insulin dosage, wherein the collection device comprises a meter configured to measure one or more selected biomarkers, a processor disposed inside the meter and coupled to a memory, wherein the memory stores the structured collection procedure provided from the server, and software having instructions that when executed by the processor causes the processor to instruct the diabetic person to collect one or more sampling sets of biomarker data in accordance with the structured collection procedure, wherein the server is a central repository for a plurality of the structured collection procedures;
collecting one or more sampling sets of biomarker data by the collection device, wherein each of the one or more sampling sets comprises a plurality of sampling instances recorded over a collection period and each sampling instance of the plurality of sampling instances comprises an acceptable biomarker reading recorded upon compliance with one or more acceptance criterion based on at least one of a schedule-based action or a patient-based action and that is applied to the one or more sampling sets of biomarker data, wherein the one or more acceptance criterion require collection of the acceptable biomarker reading by the diabetic patient at a time required by the collection device;
wherein after each collection of the one or more sampling sets of biomarker data, said processor performs the processes of:
calculating a biomarker sampling parameter from the one or more sampling sets of biomarker data and as a function of only these biomarker data that are in compliance with the one or more acceptance criterion;
comparing the biomarker sampling parameter to a target biomarker range;
calculating an insulin adjustment parameter associated with the biomarker sampling parameter in response to the biomarker sampling parameter falling outside the target biomarker range;
adjusting an insulin dosage by an amount of the insulin adjustment parameter in response to the biomarker sampling parameter falling outside the target biomarker range and in response to the insulin dosage not exceeding maximum dosage; and exiting the testing method in response to the adjusted insulin dosage being optimized as an optimized insulin dosage such that the optimized insulin dosage is administered as the administered insulin dosage, otherwise repeating with a next sampling set of the one or more sampling sets of biomarker data, the optimized insulin dosage being achieved when the one or more biomarker sampling parameters fall within the target biomarker range.

\* \* \* \* \*